US011697958B1

(12) United States Patent
Weinerman et al.

(10) Patent No.: US 11,697,958 B1
(45) Date of Patent: *Jul. 11, 2023

(54) APPARATUS FOR CONTROLLING BUS DOORS

(71) Applicant: The Eastern Company, Strongsville, OH (US)

(72) Inventors: Lee S Weinerman, Medina, OH (US); Marinel Rosu, Strongsville, OH (US); Reese Bernot, Strongsville, OH (US); Keith Braun, Strongsville, OH (US); James Paxitzis, Strongsville, OH (US)

(73) Assignee: The Eastern Company, Cleveland, OH (US)

( * ) Notice: Subject to any disclaimer, the term of this patent is extended or adjusted under 35 U.S.C. 154(b) by 75 days.

This patent is subject to a terminal disclaimer.

(21) Appl. No.: 17/158,606

(22) Filed: Jan. 26, 2021

Related U.S. Application Data

(60) Provisional application No. 62/967,840, filed on Jan. 30, 2020.

(51) Int. Cl.
*E05F 15/00* (2015.01)
*E05F 15/40* (2015.01)
(Continued)

(52) U.S. Cl.
CPC ............. *E05F 15/40* (2015.01); *B60J 5/0477* (2013.01); *B60J 5/0497* (2013.01); *B60Q 5/005* (2013.01);
(Continued)

(58) Field of Classification Search
CPC ......... E05F 15/40; E05F 15/616; E05F 15/72; E05F 15/76; E05F 17/004; E05F 2017/008; B60Q 5/005
(Continued)

(56) References Cited

U.S. PATENT DOCUMENTS 2,789,813 A * 4/1957 Runkle .................. E05F 15/53
49/141
4,375,140 A * 3/1983 Blair .................... E05F 17/004
49/108
(Continued)

FOREIGN PATENT DOCUMENTS

DE 102016211054 A1 * 12/2017
JP 2005296315 * 10/2005 ........ E05F 2017/008

OTHER PUBLICATIONS

English translation of the JP2005296315 (Year: 2005).*

*Primary Examiner* — Janet M Wilkens
*Assistant Examiner* — Daniel Alvarez
(74) *Attorney, Agent, or Firm* — Ralph E. Jocke; Walker & Jocke

(57) ABSTRACT

An apparatus for controlling bus doors (14, 16) that are arranged as a pair of doors that move in coordinated relation between door open positions and door closed positions, enables passengers to access an interior area (12) of a bus (10). The apparatus includes an actuator (28, 226). The actuator includes a drive lever (34, 228) that is selectively rotationally movable between rotational positions in which both of the doors are in the open positions and in the closed positions. Exemplary arrangements include at least one controller (128) that is operative to prevent the doors from causing damage to or from being damaged by engagement with obstructions. The controller further enables a bus driver or other authorized user to control access to the interior area of the bus using a user mobile device (144).

34 Claims, 31 Drawing Sheets

(51) Int. Cl.
  *B60J 5/04*    (2006.01)
  *E05F 15/616*  (2015.01)
  *E05F 15/72*   (2015.01)
  *E05F 15/76*   (2015.01)
  *E05F 11/32*   (2006.01)
  *H04N 7/18*    (2006.01)
  *H04W 4/12*    (2009.01)
  *H04W 4/42*    (2018.01)
  *G01N 33/00*   (2006.01)
  *B60Q 5/00*    (2006.01)
  *E05F 17/00*   (2006.01)
  *E05F 15/53*   (2015.01)
  *E05F 15/73*   (2015.01)

(52) U.S. Cl.
  CPC ............ *E05F 11/32* (2013.01); *E05F 15/616* (2015.01); *E05F 15/72* (2015.01); *E05F 15/76* (2015.01); *E05F 17/004* (2013.01); *G01N 33/004* (2013.01); *H04N 7/185* (2013.01); *H04W 4/12* (2013.01); *H04W 4/42* (2018.02); *E05F 15/53* (2015.01); *E05F 2015/767* (2015.01); *E05F 2017/008* (2013.01); *E05Y 2201/434* (2013.01); *E05Y 2201/454* (2013.01); *E05Y 2201/626* (2013.01); *E05Y 2201/726* (2013.01); *E05Y 2400/36* (2013.01); *E05Y 2400/44* (2013.01); *E05Y 2400/54* (2013.01); *E05Y 2400/66* (2013.01); *E05Y 2400/85* (2013.01); *E05Y 2900/506* (2013.01)

(58) Field of Classification Search
  USPC ........................................... 49/114
  See application file for complete search history.

(56) References Cited

U.S. PATENT DOCUMENTS

| | | | | |
|---|---|---|---|---|
| 4,433,505 | A * | 2/1984 | Viner | E05F 15/53 49/110 |
| 4,702,037 | A * | 10/1987 | Hollowell | E05F 17/004 49/501 |
| 6,361,430 | B2 * | 3/2002 | Kitching | E21F 1/10 454/169 |
| 9,196,146 | B1 * | 11/2015 | Vicente | G08B 21/14 |
| 10,487,566 | B2 * | 11/2019 | Sciulli | F16H 21/44 |
| 10,768,620 | B1 * | 9/2020 | Tran | B60R 1/00 |
| 11,091,950 | B2 * | 8/2021 | Ozaki | B61L 15/0081 |
| 11,105,139 | B2 * | 8/2021 | Junod | B60J 7/141 |

* cited by examiner

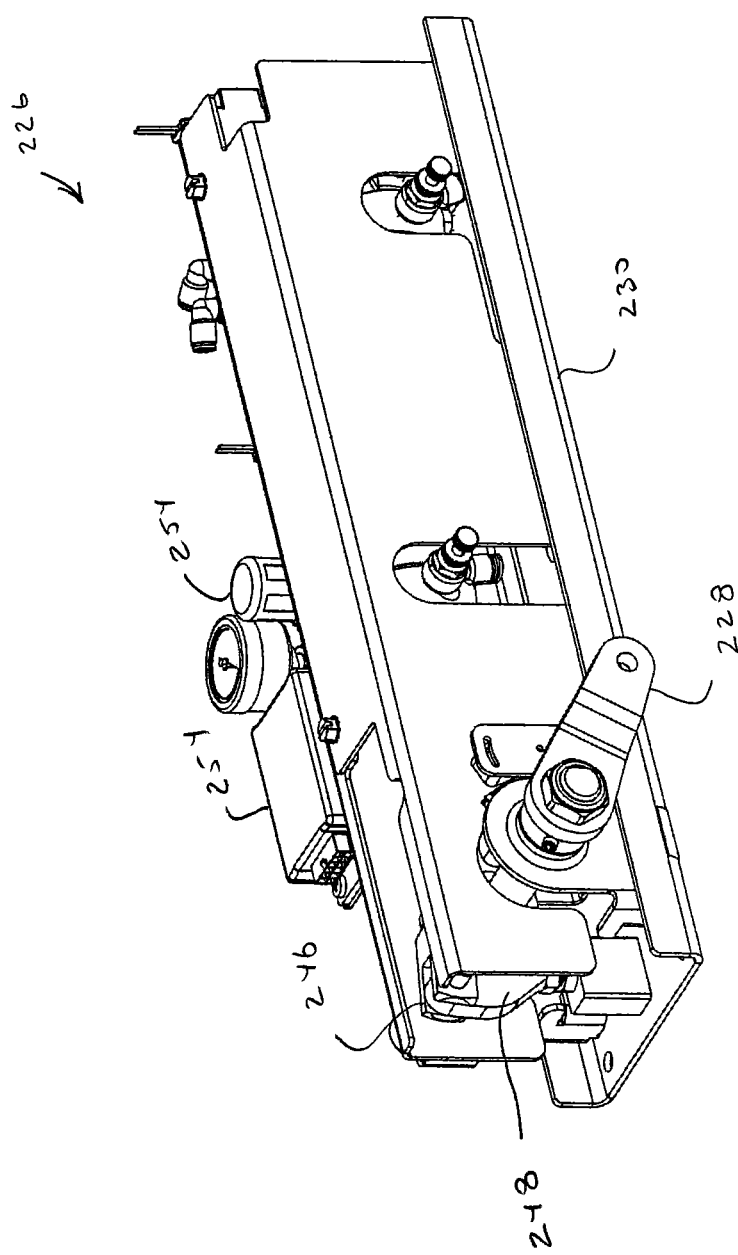

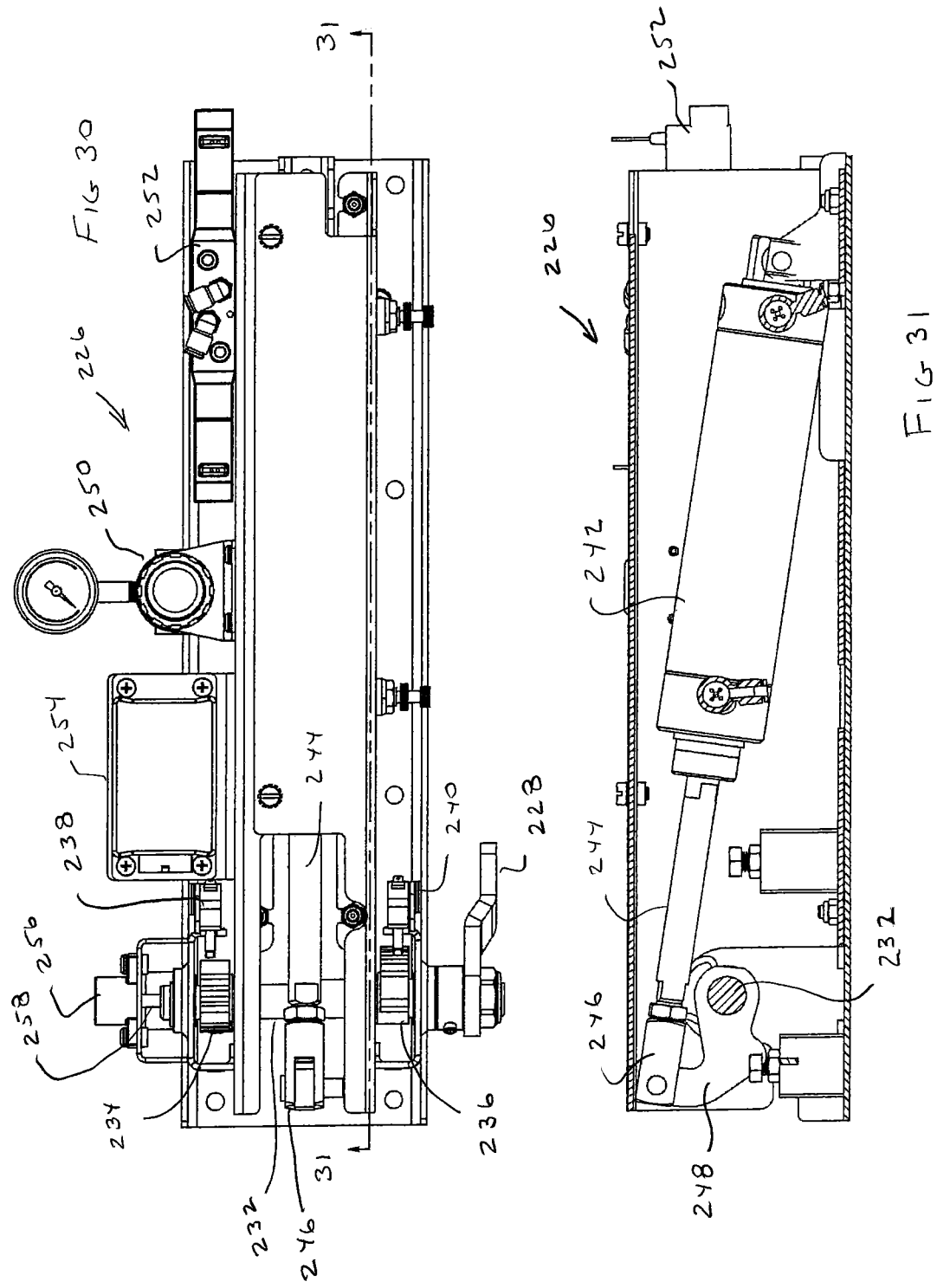

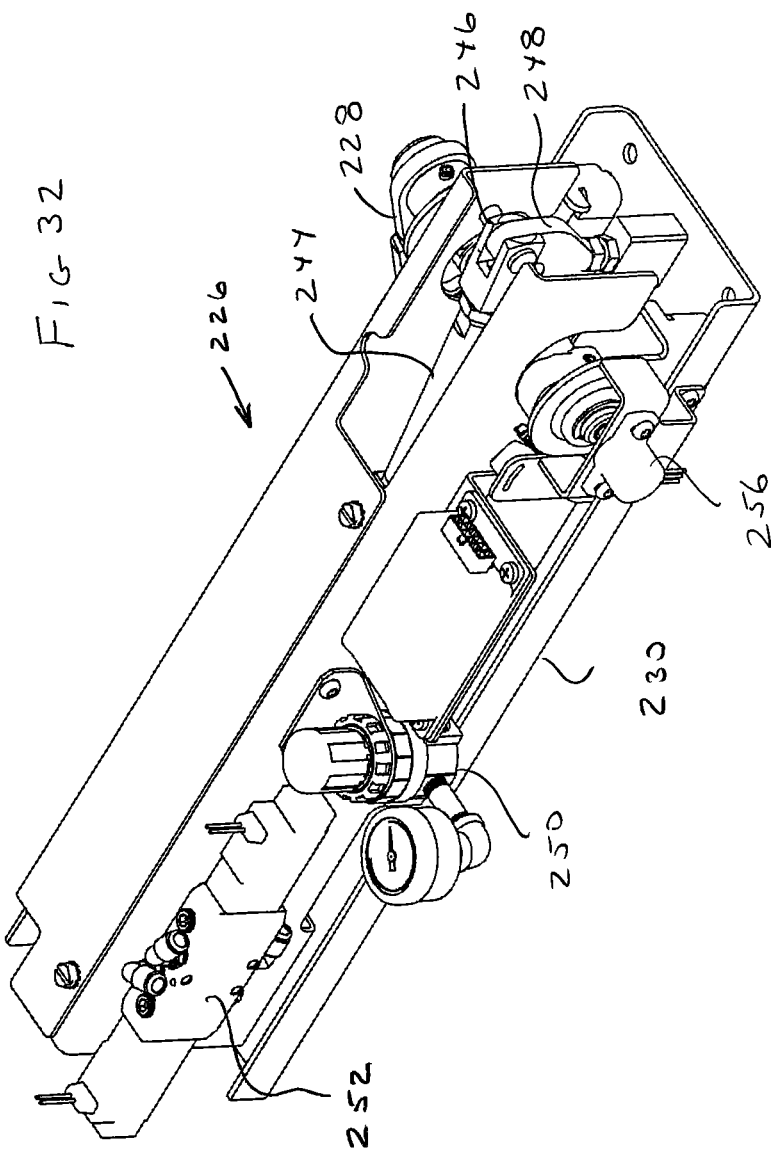

APPARATUS FOR CONTROLLING BUS DOORS

TECHNICAL FIELD

Exemplary arrangements relate to an apparatus for controlling doors which selectively enable access to an interior area of a bus or similar vehicle.

BACKGROUND

Buses and other highway vehicles that provide transportation for significant numbers of persons (all of which vehicles will be referred to herein as a bus for brevity) commonly have at least one path by which persons may enter and leave the interior area of the bus. Some such vehicles have a pair of rotatable doors that operate in coordinated relation to move between respective open and closed positions under the control of a bus driver or other operator. When each of the doors in the pair is in the respective open position, passengers are enabled to enter or leave the interior area of the bus by moving along the path. When each of the doors in the pair is in the closed position, the path is blocked by the doors and passengers are not able to enter or leave the bus by moving along the path.

Sometimes the bus driver or other operator is not able to see a person or an obstruction that may be in the path when the doors in the pair are in the open positions. As a result the bus driver may try to close the doors striking the person or object. This may cause injury to the person and/or damage to the doors or the object.

The bus driver may sometimes have to leave the interior area of the bus to attend to other matters. The bus driver may need to leave the doors unlocked so that the bus driver can get back into the interior area of the bus when they return. If the bus driver has gone somewhere where the bus is out of the driver's sight, the driver may be concerned that unauthorized persons may have entered the bus while the driver was away. Also in some circumstances, the bus driver may want to leave the bus running while the driver is away. The driver may want to do this during cold conditions so that the interior of the bus remains warm, or alternatively the bus driver may want to do this in hot conditions so that the air conditioning continues to run and the interior area of the bus remains cool.

Apparatus for controlling the doors of a bus or similar vehicle may benefit from improvements.

SUMMARY

Exemplary arrangements provide an apparatus that is usable to control a pair of doors that control passenger access through a path that may be used for entering or leaving a bus or similar vehicle. In exemplary arrangements an actuator is in operative connection with the pair of doors and enables a bus driver or other operator within the vehicle to selectively cause the doors to move in coordinated relation between door closed positions in which the path is blocked, and door open positions in which the path is open.

Exemplary arrangements may provide for the doors to automatically reverse direction in situations where a door that is moving between the open position and the closed position encounters an object. In alternative arrangements, a door moving between the closed position and the open position may reverse direction when an object is encountered in moving toward the open position. In this way the risk of injury to persons or damage to the doors or other objects may be minimized.

In other exemplary arrangements a bus driver or other operator is able to control the doors from outside the vehicle through wireless communication using a driver's mobile device. In some arrangements the bus driver is enabled to secure the doors in the closed position from outside the bus when the driver has left the interior area the bus. The driver can also open the doors using the mobile device upon the return of the driver to be in proximity of the bus and/or in other circumstances. In some exemplary arrangements the bus driver who is away from the bus is able to monitor certain conditions and persons in proximity to the bus using the mobile device. Numerous other features and capabilities may be provided in exemplary arrangements.

BRIEF DESCRIPTION OF DRAWINGS

FIG. 29 is a back bottom left perspective view of an alternative actuator that may be utilized for controlling a pair of doors that control access to an interior area of a bus or similar vehicle.

FIG. 30 is a back view of the alternative actuator shown in FIG. 29.

FIG. 31 is a sectional view taken along line 31-31 in FIG. 30.

FIG. 32 is a back top left perspective view of the alternative actuator.

DETAILED DESCRIPTION

Figure 1:
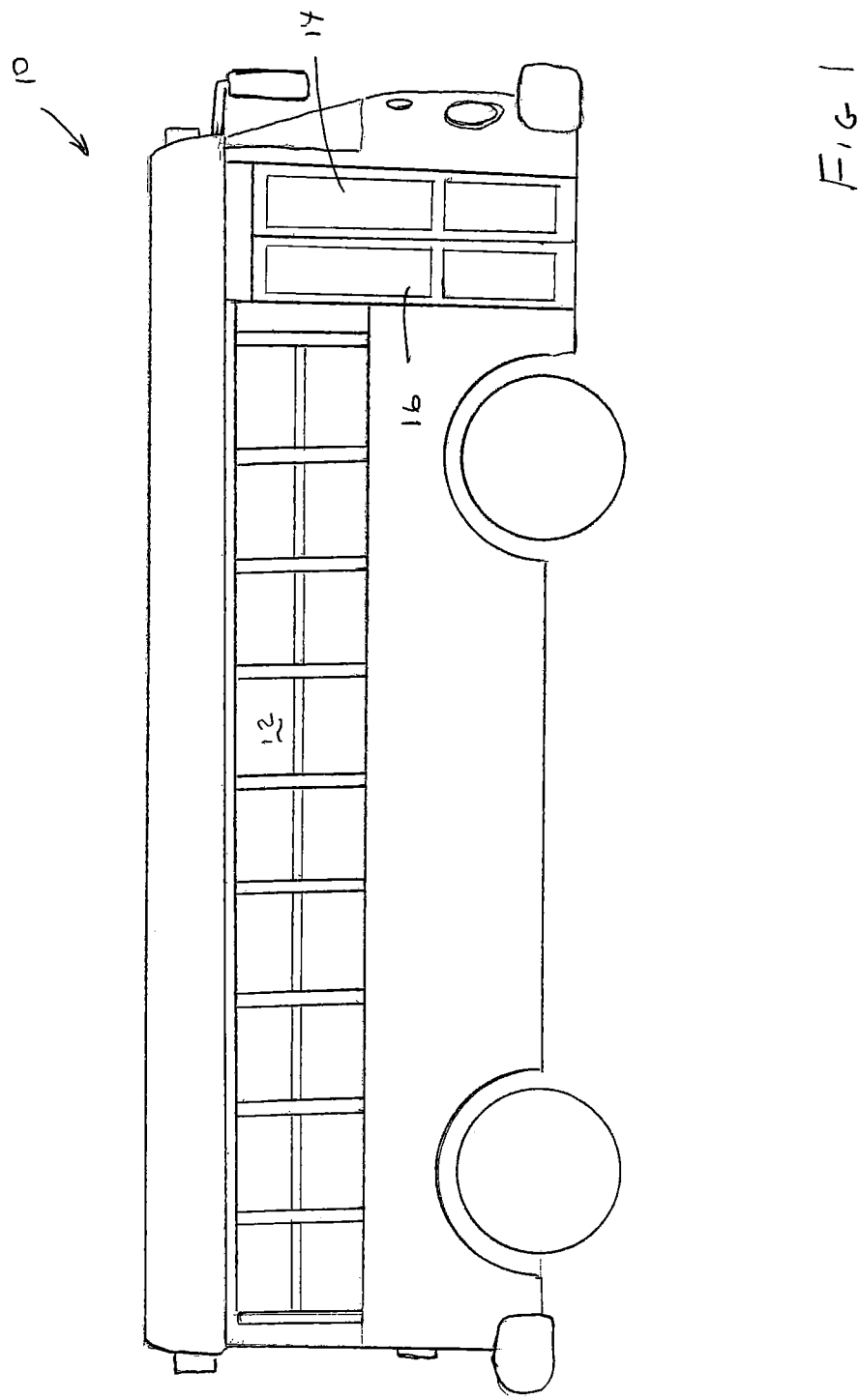
FIG. 1 is a side view of an exemplary multi passenger highway transport vehicle such as a bus, which includes a pair of doors that control passenger access to and from an interior area of the vehicle through a path, each of the doors being shown in the door closed position.
Figure 2:
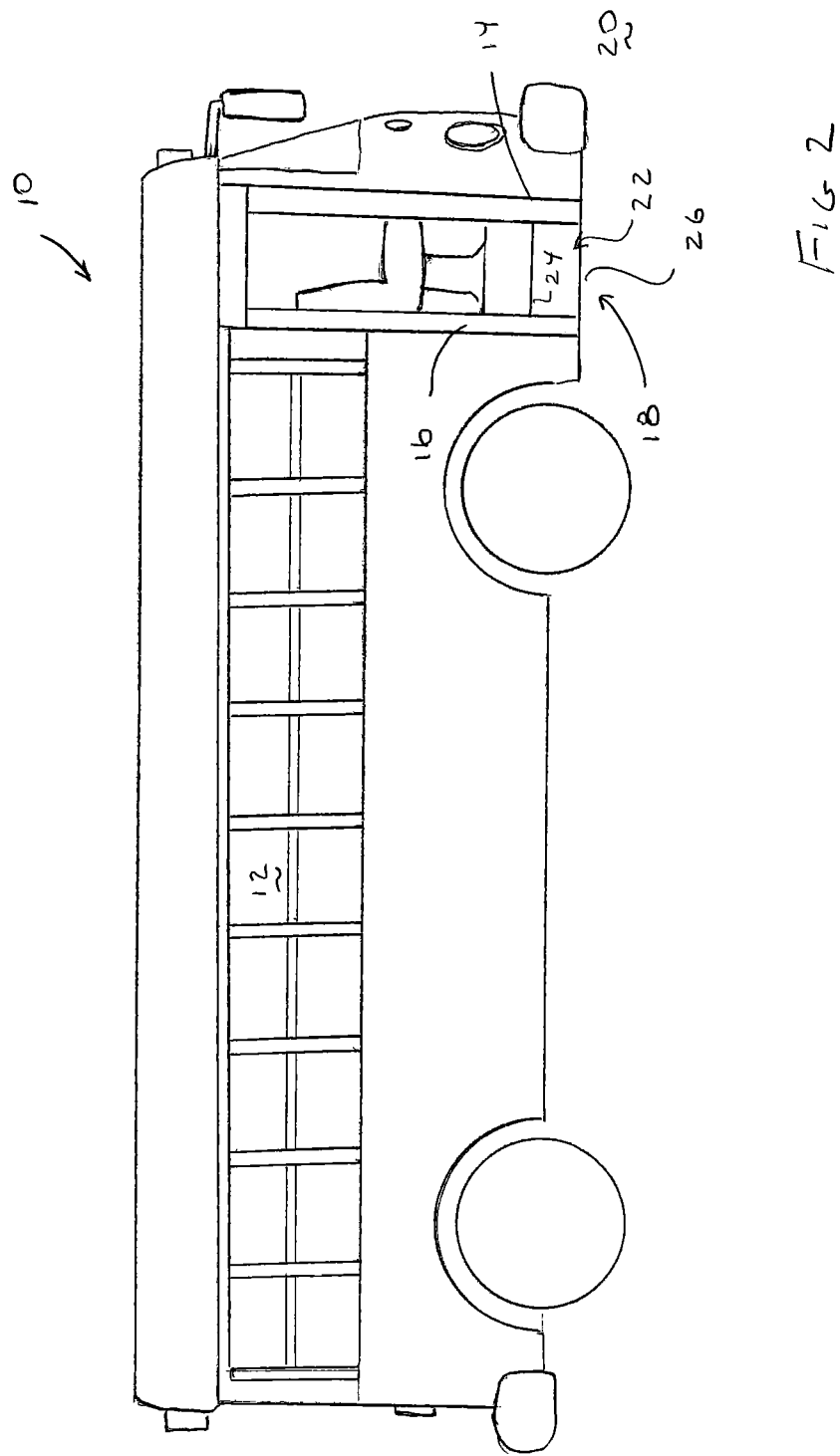
FIG. 2 is a view of the bus similar to FIG. 1, but with each of the doors shown in the door open position.
Figure 3:
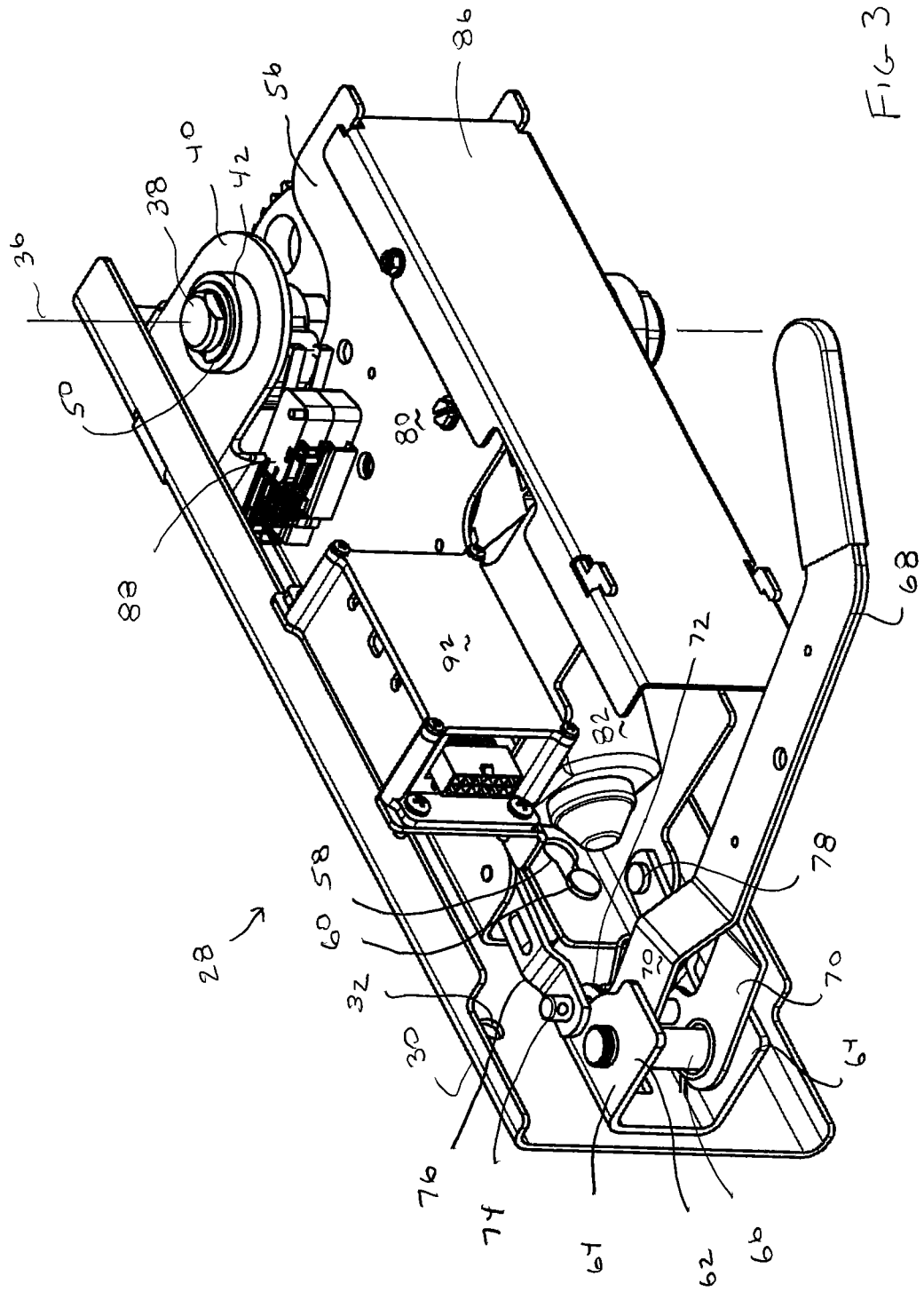
FIG. 3 is a back top left perspective view of an exemplary door actuator.
Figure 4:
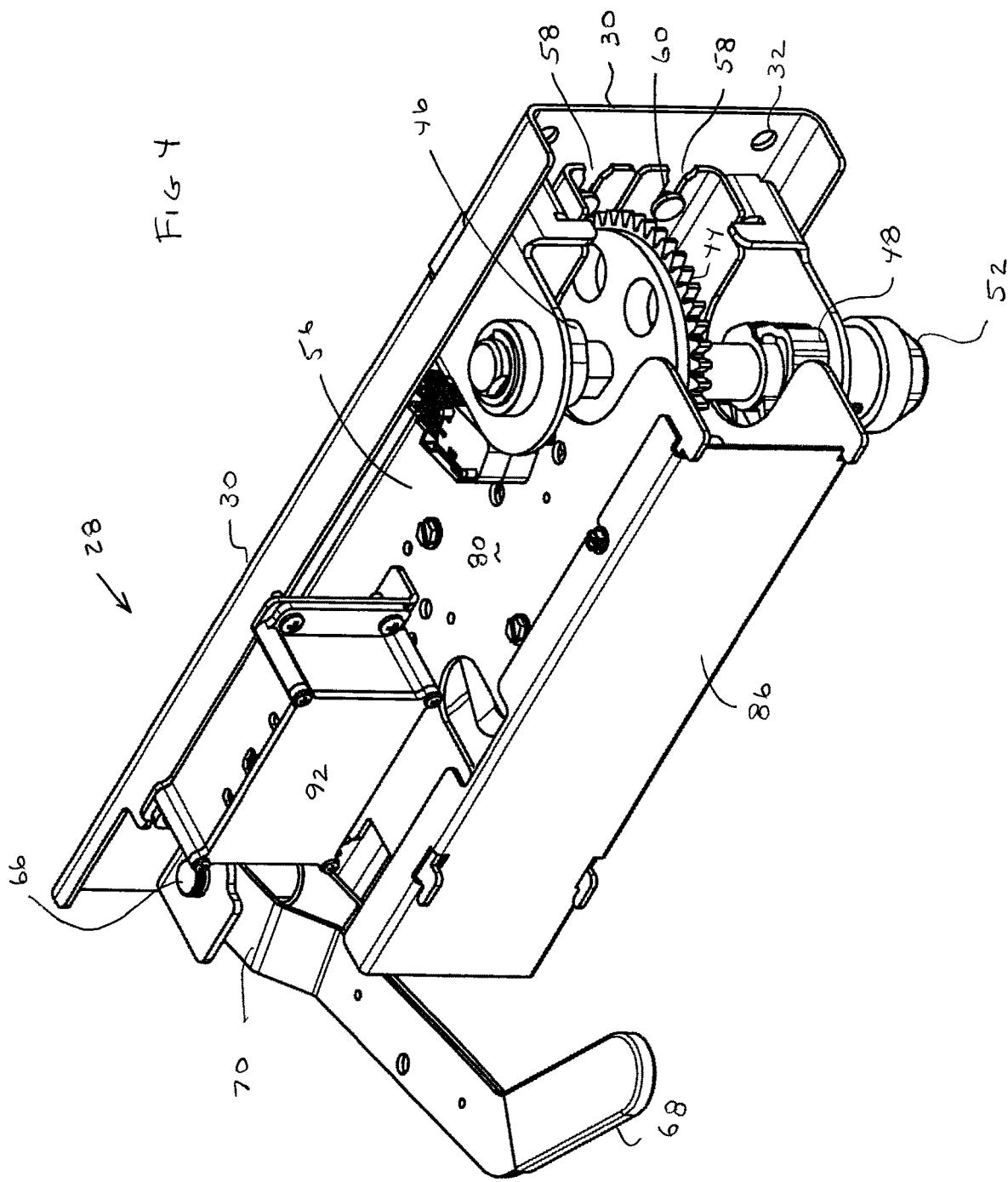
FIG. 4 is a back top right perspective view of the door actuator.
Figure 5:
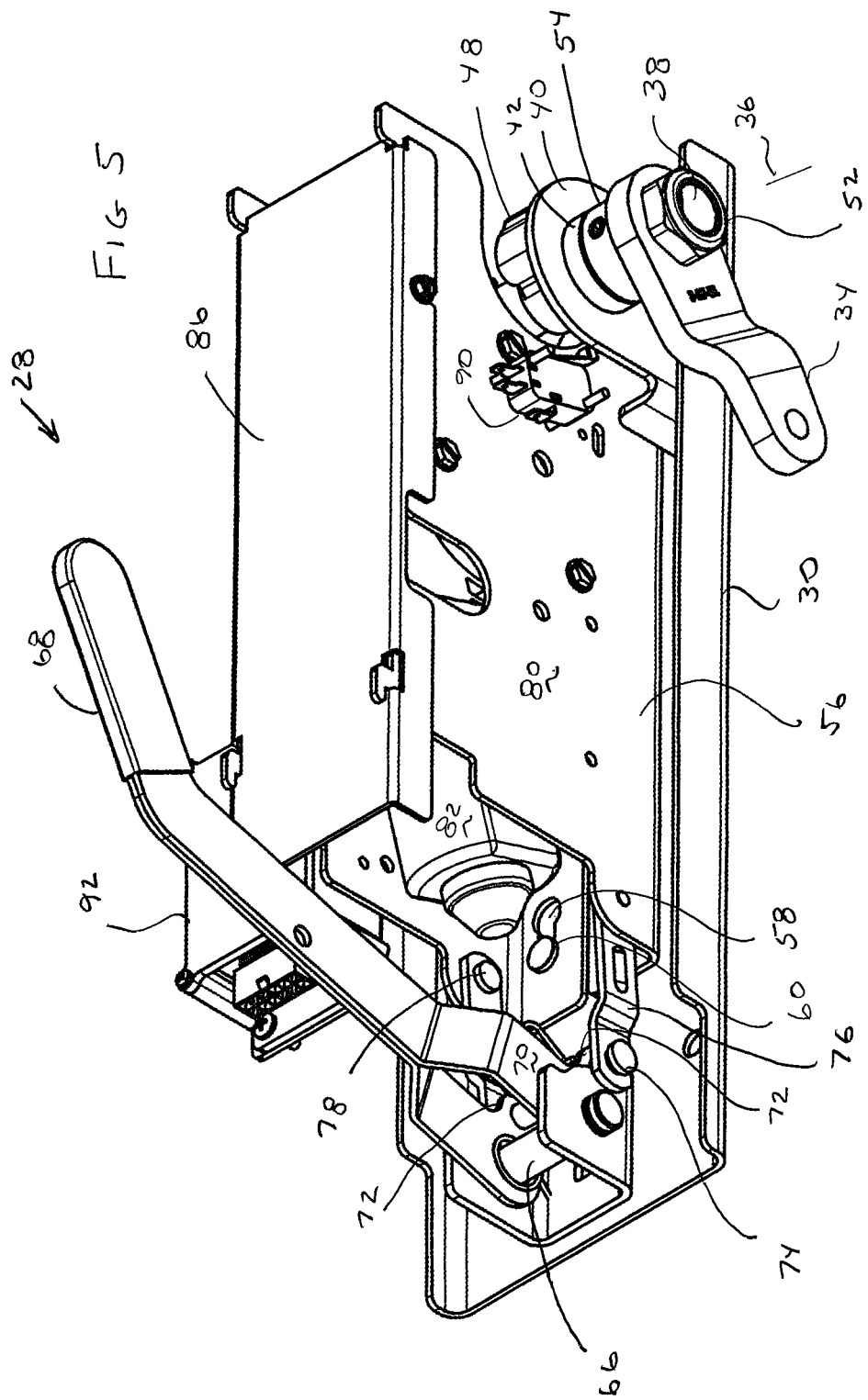
FIG. 5 is a back bottom left perspective view of the door actuator.
Figure 6:
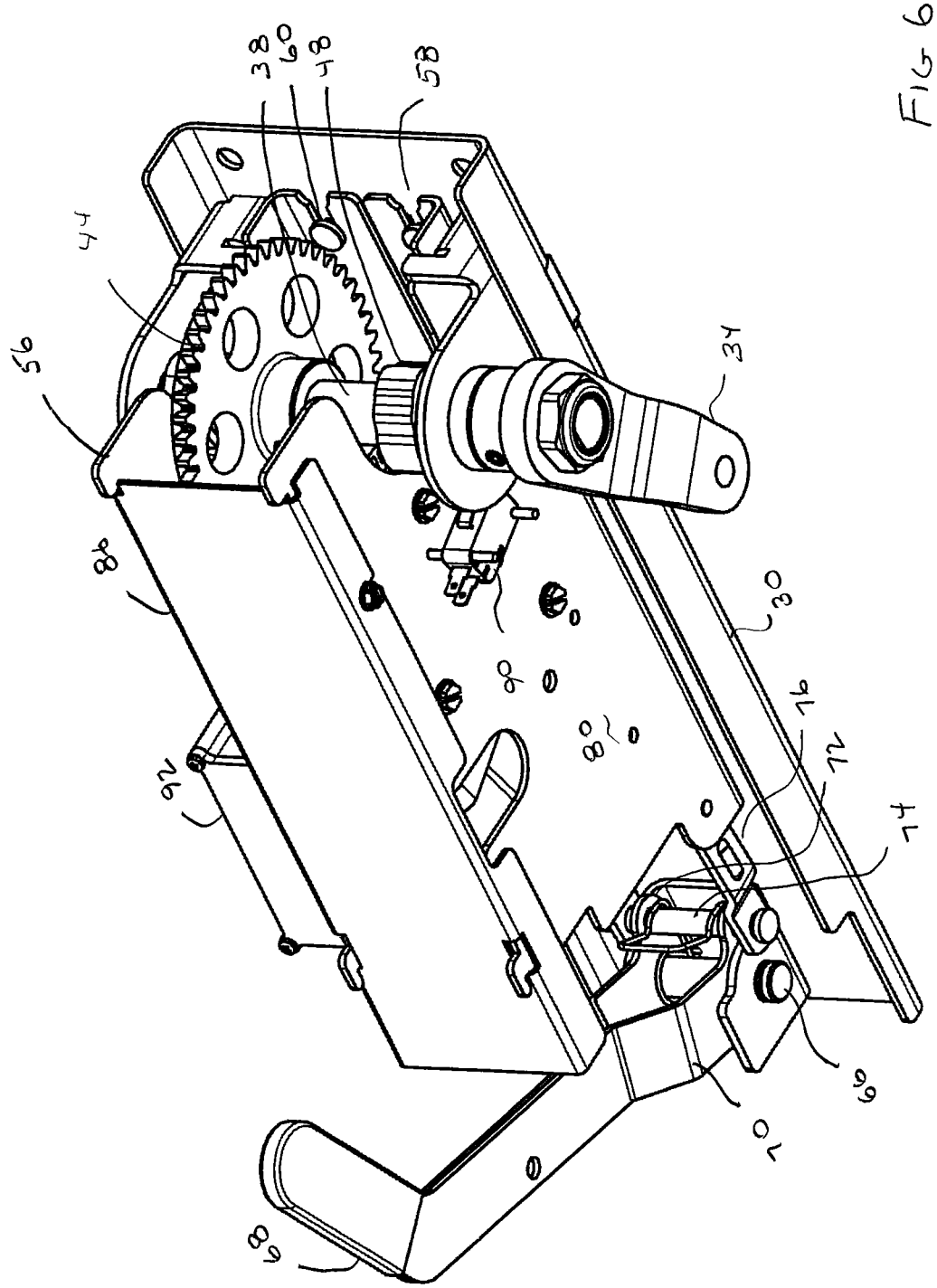
FIG. 6 is a back bottom right perspective view of the door actuator.

Referring now to the drawings and particularly to FIG. 1, there is shown therein an exemplary highway vehicle that provides transportation for a plurality of persons in the form of a bus 10. The exemplary bus 10 includes an interior area 12 that is configured to house a bus driver and a plurality of passengers. Access to the interior area of the bus is controlled by a pair of substantially planar doors 14, 16. When used herein substantially planar means that a majority of a surface of a structure extends in a common plane. The pair of doors 14, 16 are rotatably movable from the closed positions of the doors shown in FIG. 1 to the open positions of the doors that is shown in FIG. 2.

In the exemplary arrangement the interior area 12 of the bus 10 is accessed by passengers who move along a path 18 from an exterior area 20 of the bus into the interior area 12. In the exemplary arrangement the path 18 includes an entry area 22 which is proximate to the space occupied by the doors 14, 16 in the closed positions. The exemplary path 18 includes a pair of steps 24, 26. In the exemplary arrangement passengers travel along the path 18 up the steps 24, 26 to reach seats located in the interior area 12 of the bus. Likewise, when passengers exit the bus they travel down the steps 24, 26 to exit from the interior area 12. As shown in FIG. 2 with the doors 14, 16 in the open positions, the doors extend substantially parallel to one another and bound the opposed sides of the open path 18 along which passengers travel when entering and exiting the bus. As used herein when it is stated that the doors extend substantially parallel to one another it means that the substantially planar surfaces of the doors that bound the interior area of the bus in the door closed positions, extend parallel to each other plus or minus 20°.

In the exemplary arrangement shown, the bus includes only one pair of doors that are commonly used by passengers to enter and leave the interior area of the bus under normal circumstances. It should be appreciated that the bus may include other doors such as emergency exit doors and hatches that may be used in unusual circumstances. It should be understood that in other arrangements a bus may include additional pathways and doors that can be used by passengers to enter and exit the bus. This may include pairs of doors that are located at locations such as at the midsection of the bus and/or at the rear of the bus. Other exemplary arrangements may include doors on other transverse sides of the bus or in other locations. In the exemplary arrangement, the open and closed positions of the doors are controlled by a bus driver or other operator located in the interior area of the bus. The bus driver may control the condition of the doors by manual actuation of one or more manually actuatable switches in a manner like that hereinafter described. Of course it should be understood that these approaches are exemplary and in other arrangements other approaches may be used.

In some exemplary arrangements the doors 14, 16 are moved in coordinated relation between the open positions and the closed positions by an actuator. An exemplary actuator 28 is shown in FIGS. 3-8. Exemplary actuator 28 is configured to be mounted within the interior area 12 of the bus above the pair of doors 14, 16 in a manner like that later discussed. The exemplary actuator 28 includes a body 30. The body 30 is configured to be attached in fixed relation to a header or other structural member within the bus by fasteners that extend through apertures 32. The actuator 28 further includes a drive lever 34. The drive lever 34 is rotatably movably mounted in operative supported connection with the body 30 and is rotatable about an axis 36. The drive lever 34 is in fixed operative connection with a shaft 38. The shaft extends through a pair of outward extending ears 40 that are in operative connection with the body. A respective bushing 42 is mounted in operative connection with each ear. The shaft 38 is rotationally movable in each bushing 42.

The exemplary shaft 38 is in fixed operative connection with a ring gear 44. The shaft 38 is also in fixed operative connection with an upper cam 46 and a lower cam 48. As later discussed the upper cam 46 and the lower cam 48 are usable in the exemplary arrangement to determine when the drive lever 34 is in at least a first rotational position which corresponds to both of the doors 14, 16 being in the open positions, and when the drive lever is in a second rotational position which corresponds to both of the doors 14, 16 being in the closed positions. In other arrangements the cams may be configured to indicate positions intermediate of the door open and door closed positions. In the exemplary arrangement the shaft 38 is engaged with a ring 50 which is operative to hold the shaft in the operative axial position. A nut 52 is used to hold the drive lever 34 in engagement with the shaft 38. A locking collar 54 is used to assure that the drive lever is secured in fixed operative rotational connection with the shaft 36. Of course it should be understood that this configuration is exemplary and in other arrangements other approaches may be used.

The exemplary actuator 28 further includes a slide 56. The exemplary slide 56 is movably mounted in operative connection with the body 30. The exemplary slide 56 includes a plurality of slotted openings 58. A plurality of guide pins 60 that are in fixed attached connection with the body 30, extend through respective slotted openings 58. The exemplary guide pins 60 each include a stem portion which extends through the slotted openings 58 and terminate outwardly in an enlarged head. This configuration enables the slide 56 to move relative to the body 30 in guided relation on the guide pins 60. Of course it should be understood that this configuration for engagement of the slide and the body is exemplary and in other arrangements other approaches may be used.

The exemplary body 30 further has in operatively fixed connection therewith a clevis bracket 62. The exemplary clevis bracket includes a pair of parallel disposed arms 64. A handle shaft 66 extends between the arms 64. A manually movable handle 68 is rotatably movable about the axis of the handle shaft 66. The exemplary handle includes a pair of disposed legs 70. Each of the legs 70 includes an opening through which the handle shaft 66 extends. Each of the legs 70 further includes a projecting portion 72. Each projecting portion 72 extends from the respective leg toward the slide 56. Each projecting portion 72 includes an opening therein through which a pin 74 extends.

The pin 74 is engaged on each transverse side with a respective slide link 76. Each slide link is rotatably engaged with a respective anchor pin 78. Each anchor pin 78 operatively connects a respective slide link 76 and a respective side wall 80 of the slide 56. In the exemplary arrangement this configuration enables rotational movement of the handle to cause movement of the slide in a manner like that later discussed.

Figure 7:
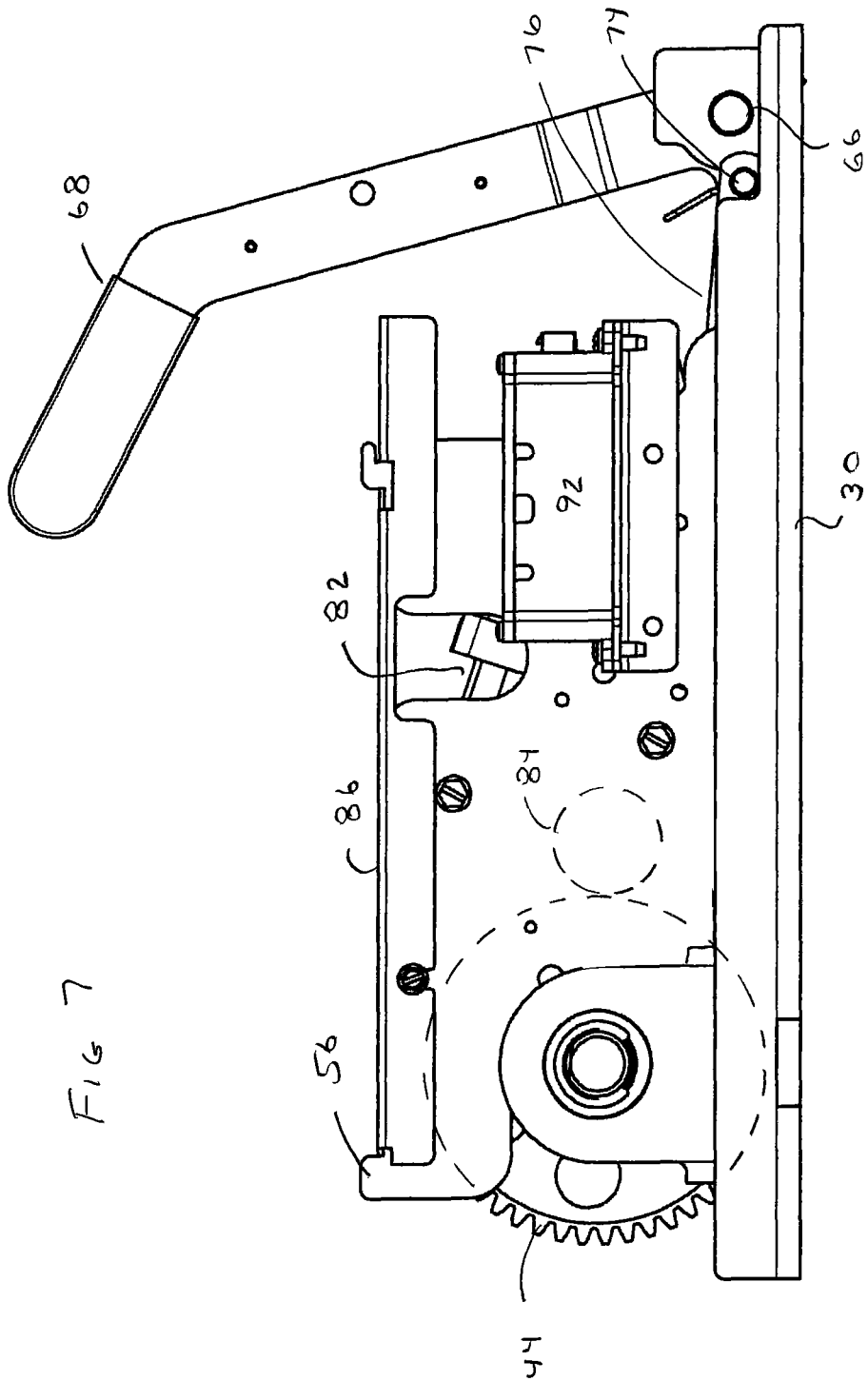
FIG. 7 is a top view of the door actuator.

In the exemplary arrangement the slide 56 has in operative attached connection therewith, a motor 82. In the exemplary arrangement shown in FIGS. 3-8 the exemplary motor is an electric motor. However it should be understood that in other arrangements other types of motors such as pneumatic motors, hydraulic motors and other types of motors that can provide controlled movement may be used. In the exemplary arrangement the motor 82 is operative to selectively rotate a pinion gear 84. The pinion gear 84 is configured to operatively engage the ring gear 44 and to cause rotation of the ring gear and the drive lever 34 attached thereto when the gears are in operatively engaged relation such as is shown in FIG. 7.

In the exemplary arrangement the slide 56 further includes a removable cover 86. The removable cover 86 is configured to enable a service user to gain access to the area located between the slide wall sides 80 including the motor positioned therein. The exemplary slide 56 further includes an upper cam switch 88. The upper cam switch in the exemplary arrangement is an electrical switch that is in attached connection with the upper wall side 80. The upper cam switch 88 is operative to detect the rotational position of the upper cam 46 and the drive lever. A lower cam switch 90 is in attached connection with the lower slide wall side 80. The lower cam switch is in operative connection with the lower cam 48. The exemplary slide 56 further has in attached connection with the upper slide wall side 80, an electrical enclosure 92. The electrical enclosure 92 may include a controller of the type later discussed in detail or other circuitry that is associated with the operation of the actuator 28.

Figure 8:
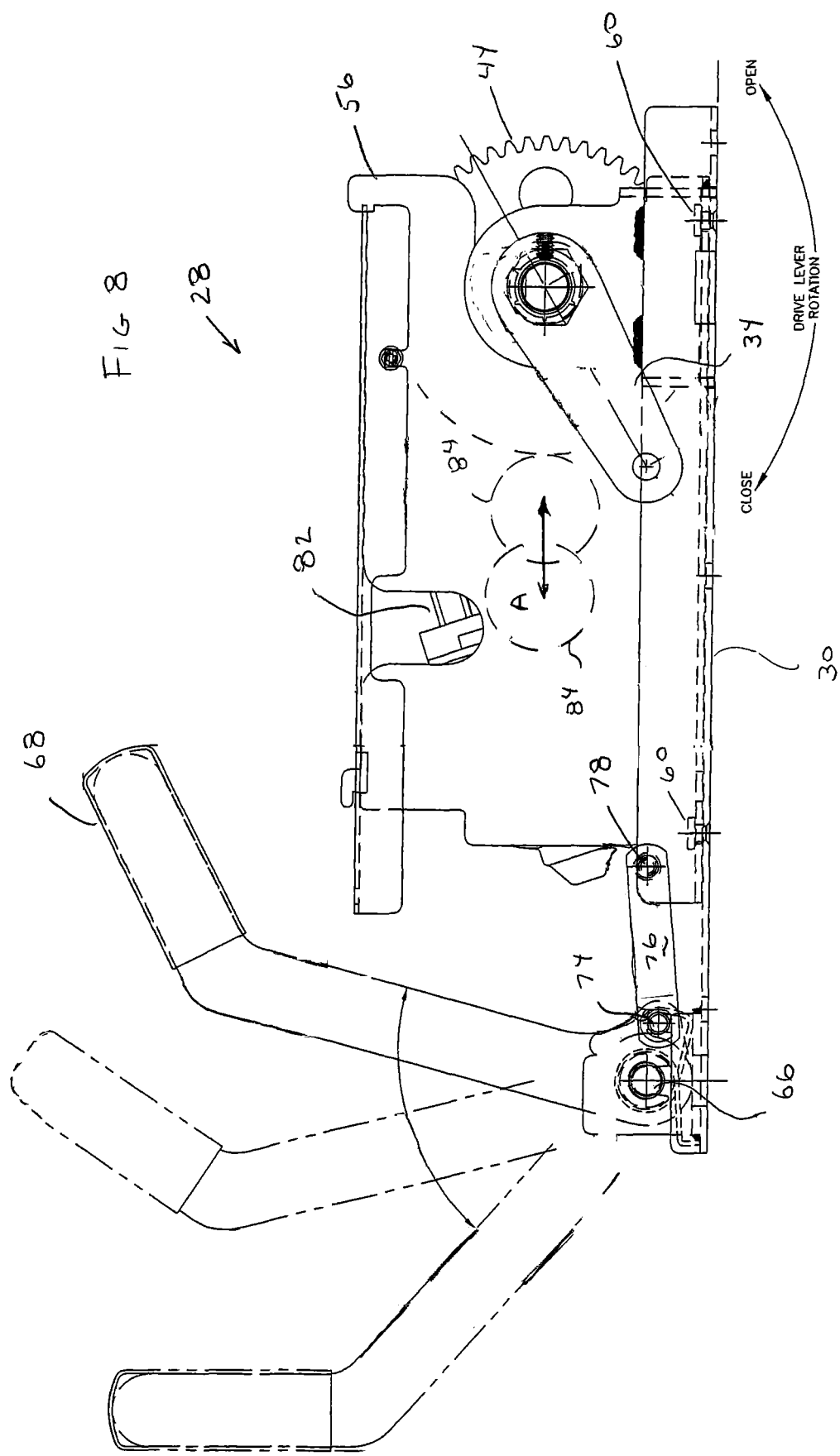
FIG. 8 is a bottom view of the door actuator showing different positions of the manually movable lever which can be used to manually operatively disengage the drive of the actuator from the doors.

As represented in FIG. 8 manual movement of the handle 68 (which is alternatively referred to herein as a lever) is operative to enable the user to move the slide 56 between a first slide position in which the motor 82 is in operative engagement with the drive lever 34 and the doors that are in operative connection therewith, and a second slide position in which the motor is operatively disengaged from the drive lever and the doors. As represented by the position of the pinion gear 84 to the right as shown in phantom in FIG. 8, when the handle 68 is in the furthest clockwise position shown, slide 56 is in a first slide position in which the pinion gear 84 is in operatively engaged meshing relation with the ring gear 44. In this engagement position, operation of the motor 82 causes rotation of the pinion gear 84, the ring gear 44 and the drive lever 34.

Movement of the handle 68 to the furthest counterclockwise position shown in FIG. 8 causes the slide links 76 to move the slide 56 to the left as shown. Such movement of the slide relative to the body 30 is operative to cause the pinion gear 84 to move along the direction of Arrow A to the position shown to the left in FIG. 8. In this second slide position the pinion gear 84 is operatively disengaged from the ring gear 44 and the drive lever 34 (and the doors 14, 16). In this disengagement position the drive lever 34 and the doors that are attached thereto, are manually movable between the door open positions and the door closed positions without resistance from the drive. As a result in the disengagement position the doors 14, 16 are enabled to be manually opened and closed even in circumstances where the actuator or other electrical circuitry associated with the system is inoperative. As a result the exemplary arrangement enables a driver or passenger of the bus to manually open or close the doors in the event of a malfunction or other problem after movement of the lever 68. Of course it should be understood that this arrangement is exemplary and other arrangements other structures and mechanisms may be utilized for operatively connecting and disconnecting a motor and the doors. However it should be understood that in some other arrangements no feature which provides this capability may be included in the actuator that is utilized to open and close the doors.

Figure 11:
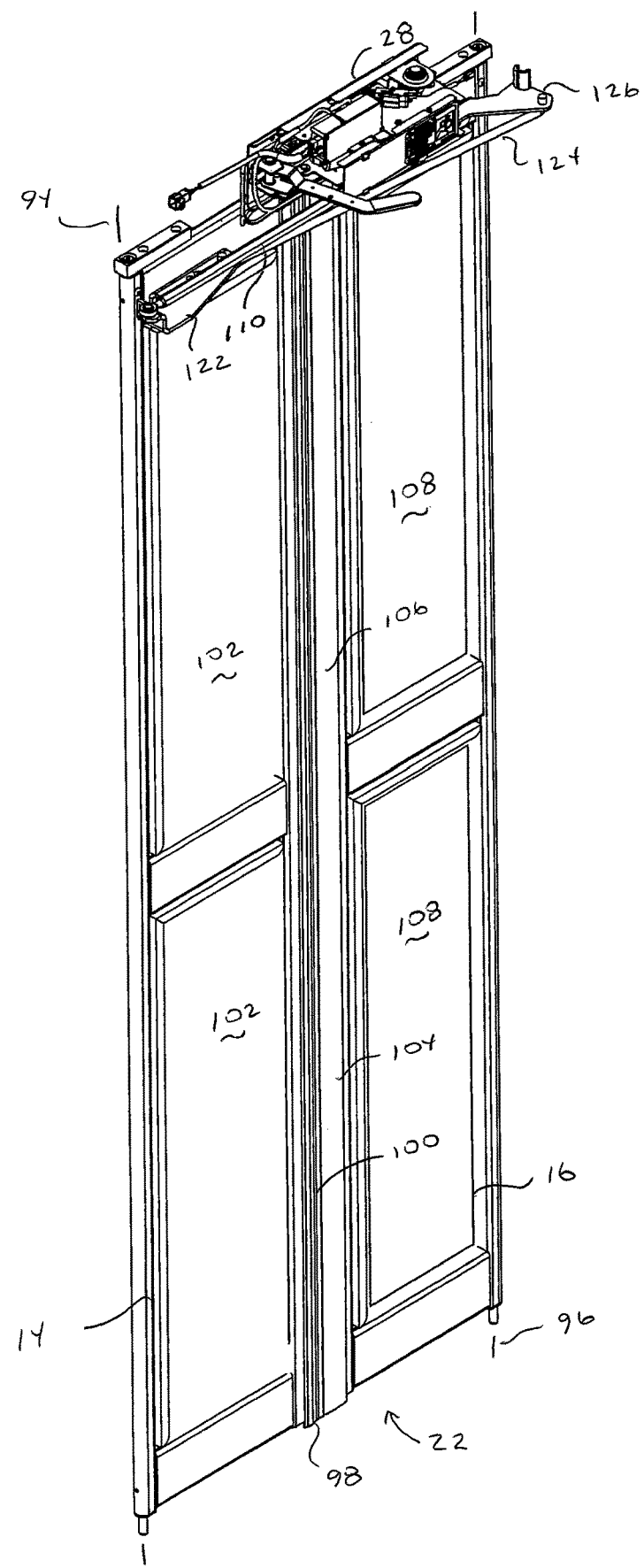
FIG. 11 is a back top left perspective view showing the exemplary actuator in operative connection with a pair of doors, each of the doors being in the door closed position.
Figure 12:
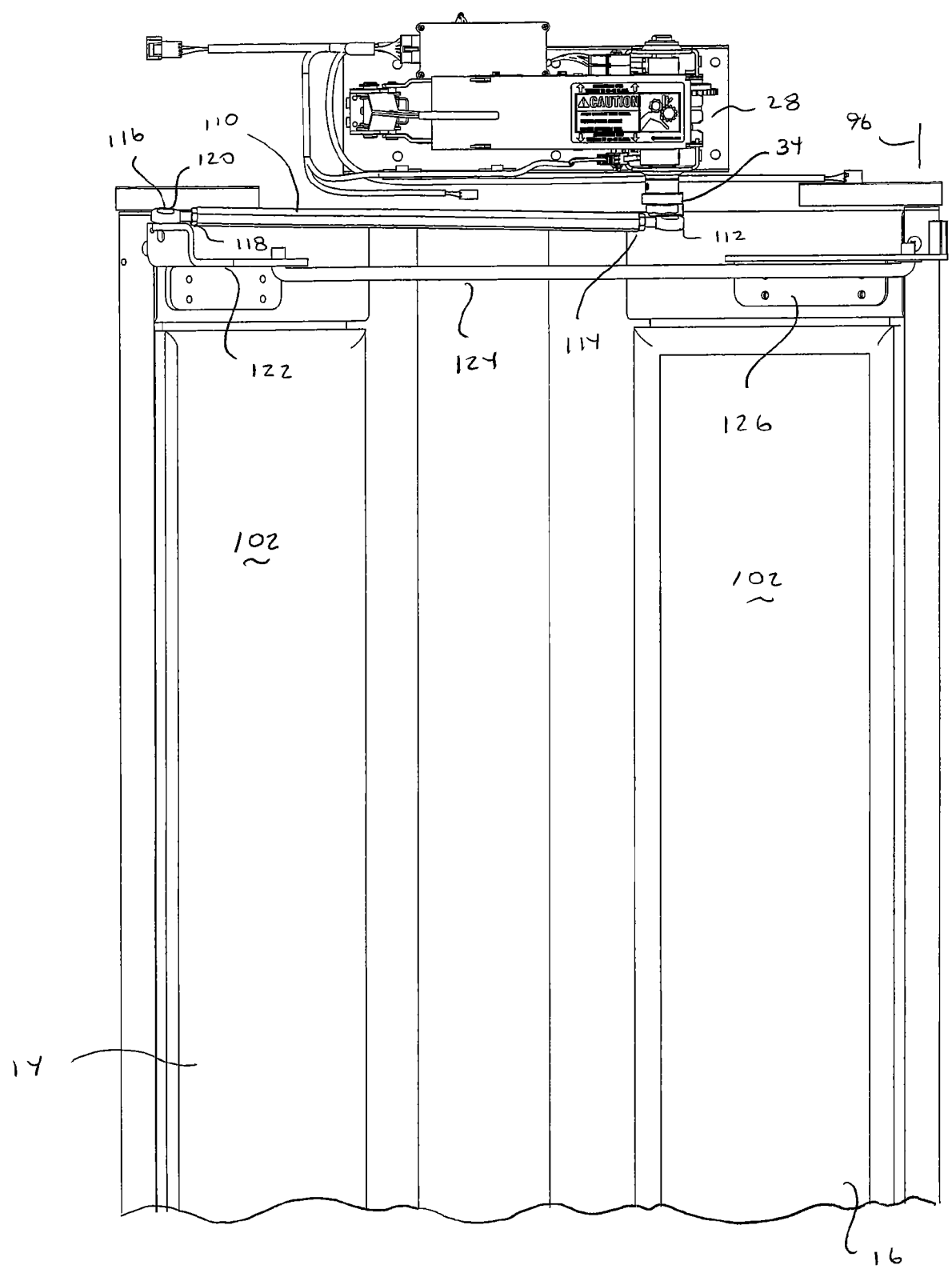
FIG. 12 is a back view of the exemplary actuator and the upper portions of the doors in the door closed positions.
Figure 13:
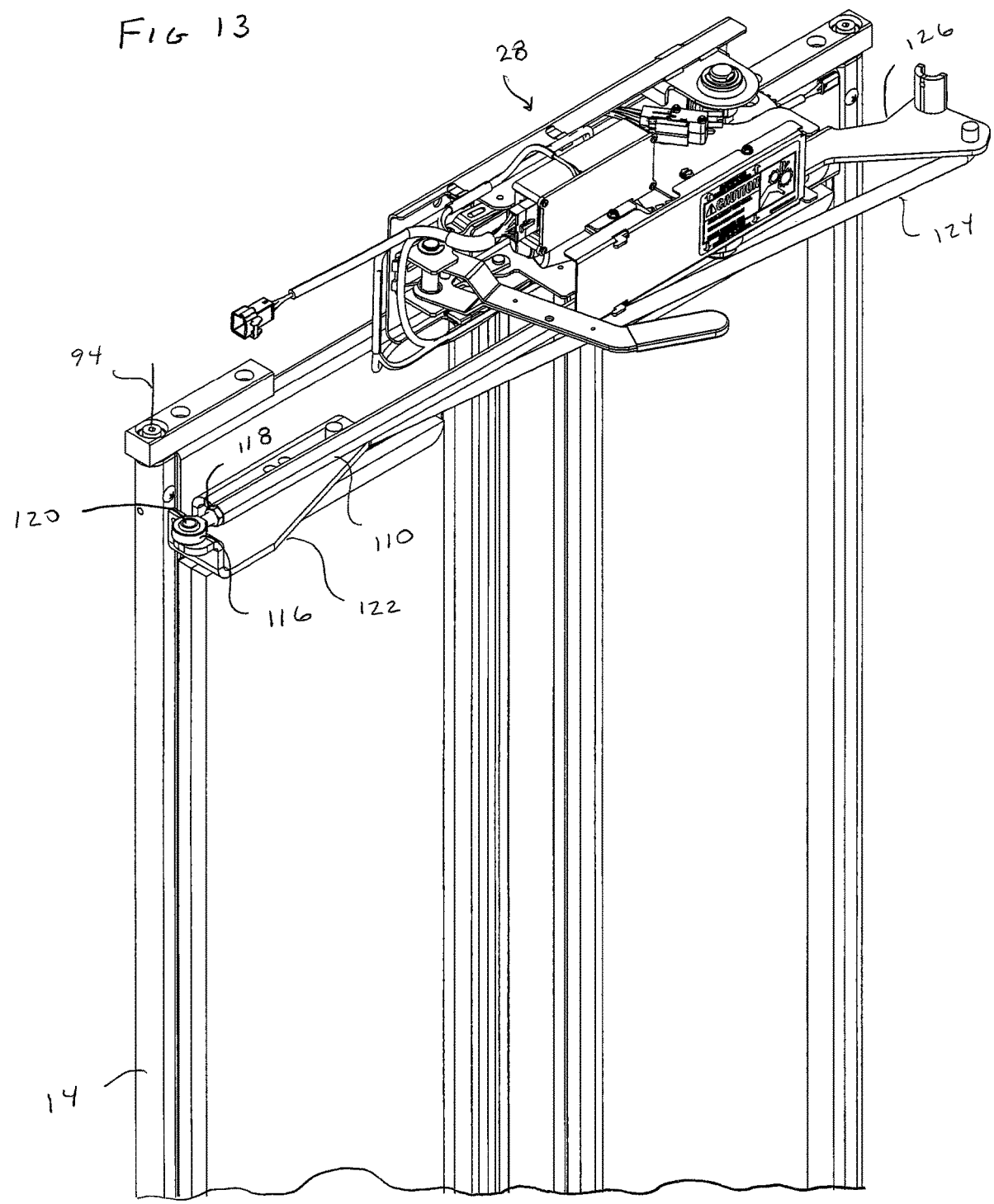
FIG. 13 is a back top left perspective view showing the actuator and the upper portions of the doors in the closed positions.
Figure 14:
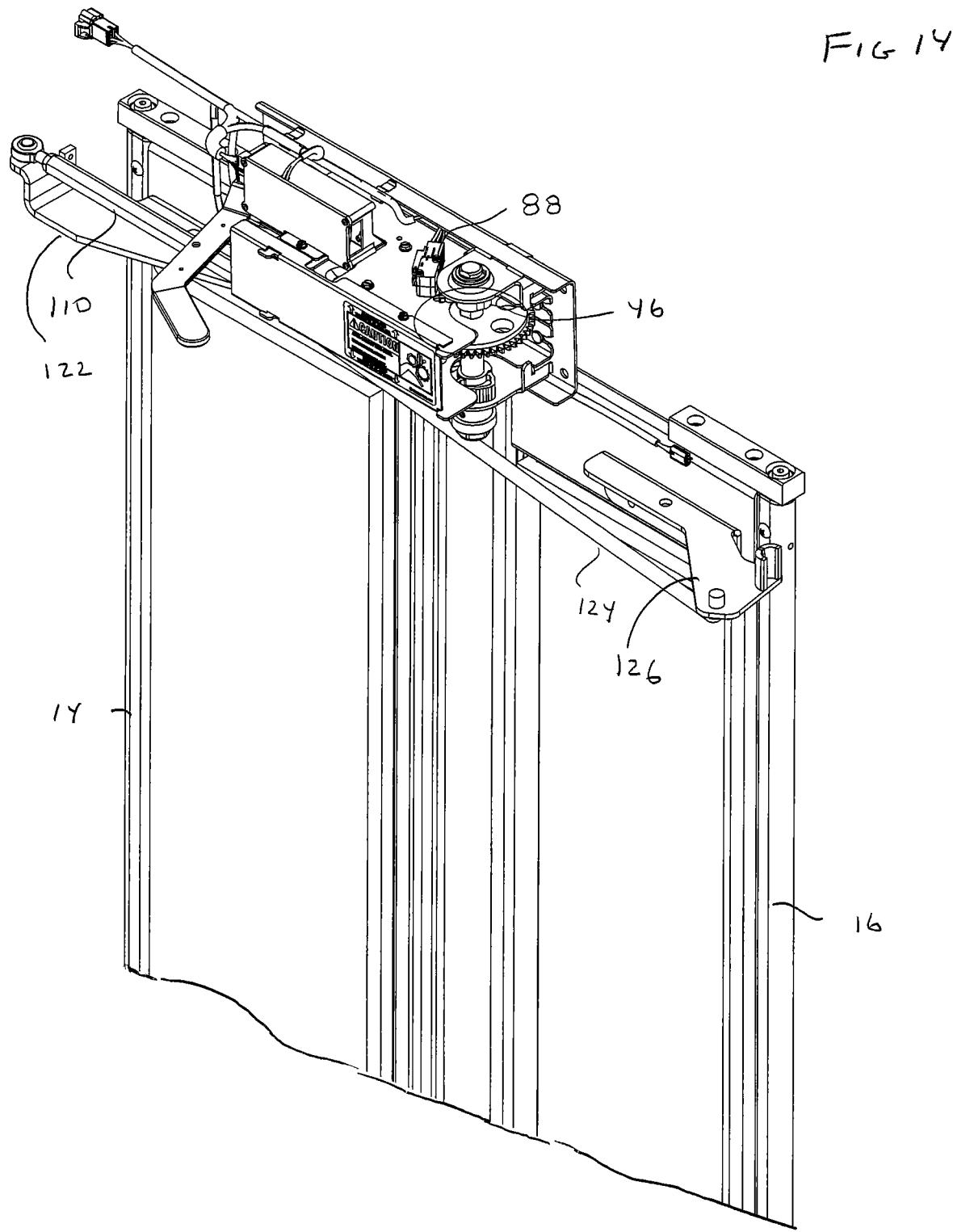
FIG. 14 is a back top right perspective view showing the actuator and the upper portions of the doors in the closed positions.

FIGS. 11-23 show the exemplary pair of doors 14, 16 in greater detail and the manner of movement thereof by the exemplary actuator 28. FIGS. 11-13 show the doors 14, 16 in the respective door closed positions. In the door closed positions the doors 14, 16 extend across the entry area 22 and block the passage of individuals along the path 18. In the exemplary door closed positions the doors 14 and 16 are substantially linearly aligned. For purposes hereof, substantially linearly aligned means that a single straight line may extend within the respective body of the majority of each of the doors 14, 16 along their transverse width. As can be appreciated in some exemplary arrangements the doors may be configured so as to block the path sufficiently to prevent ingress and egress of individuals therethrough without the entirety of the doors extending along a single straight line.

In the exemplary arrangement door 14 is rotatably movably mounted to the body of the bus about a vertical door axis 94. Door 14 is rotatable about the vertical door axis 94 which extends adjacent to the left side of the door 14 as shown. Door 16 is similarly rotatable about a vertical door axis 96. As can be appreciated axis 96 is horizontally disposed on the opposite side of the entry area 22 and the path 18 from axis 94. Exemplary door 14 includes a vertically extending side 98. Side 98 extends on the door opposite of axis 94. In the exemplary arrangement side 98 comprises an elongated resilient engaging seal 100 (See FIG. 15) to facilitate relatively airtight engagement with door 16 when the doors are in the door closed positions. The exemplary door 16 further includes a pair of vertically elongated transparent windows 102. The windows facilitate the bus driver's ability to view persons outside the door adjacent to the entry area. Exemplary door 16 likewise includes a side 104 that is transversely opposite vertical door axis 96. Side 104 includes a vertically elongated resilient seal 106 that is configured to resiliently engage seal 100 on door 14 when the doors are in the door closed positions. Door 16 also includes transparent windows 108 to facilitate viewing by the driver of the exterior area 20 and the entry area 22. Of course it should be understood that these door configurations are exemplary and in other arrangements other approaches may be used.

As shown in FIG. 12, in the door closed positions of doors 14 and 16 the drive lever 34 is in a fixed rotational position. Drive lever 34 is in operative connection with a drive link 110. Drive lever 34 is in operative connection with the drive link 110 through a rotatable link end 112. In exemplary arrangements link end 112 may include a rotatable post or bushing that enables drive link 110 to be in operative connection with the drive lever 34 in a manner that enables the link end to rotate relative to the drive lever 34 without binding. Further in exemplary arrangements the link end 112 may include a lockable threaded portion 114 which threadably engages the body of the drive link 110. In exemplary arrangements the lockable threaded portion 114 enables adjustment of the distance that the link end 112 extends outward from the body of the drive link 110. In some exemplary arrangements this feature may facilitate adjusting the effective length of the drive link to suit the movement of the doors between the open and closed positions. Of course, this arrangement is exemplary and in other arrangements other adjustment approaches may be used.

Drive link 110 has a link end 116 at the end opposite link end 112. Link end 116 also has a lockable threaded portion 118 adjacent thereto to provide adjustment of the effective length of the drive link 110. Link end 116 is in operative rotatable connection with a connecting post 120 that extends upwardly from a bracket 122 which is attached to door 14. As shown in FIG. 12 bracket 122 is attached to door 14 above the upper window 102. Connecting post 120 is inwardly disposed on door 14 from the vertical door axis 94 thereof. As a result, movement of drive link 110 by the drive lever 34 is operative to cause movement of bracket 122 in a manner that causes door 14 to rotate about axis 94.

Bracket 122 is further in rotatable connection with a connecting rod 124. Connecting rod 124 is rotatably engaged with bracket 122 and is rotatable in an opening that extends therein. A bracket 126 is in attached operative connection with door 16 above the upper window 102 therein. Connecting rod 124 is in operative connection with bracket 126 and extends in rotatable relation in an opening therein. As can be appreciated, the upward extending ends of connecting rod 124 include suitable pins, projections or other suitable fasteners to maintain the upward extending ends in rotatably movable position within the openings of the respective brackets 122, 126.

As can be appreciated when the drive lever 34 is in the rotatable position corresponding to the door closed positions of doors 14 and 16, the connection of the doors through the connecting rod 124 and drive link 110 to the actuator 28 prevents movement of the doors. This is because (provided slide 56 is in the engagement position) the motor 82, the pinion gear 84 and the ring gear 44 operate to resist any unwanted movement of the drive lever 34. Further in the exemplary arrangement with the doors in the closed positions the configuration of the upper cam 46 causes the upper cam switch 88 to detect that the drive lever is in a rotational position which corresponds to the door closed positions.

Figure 15:
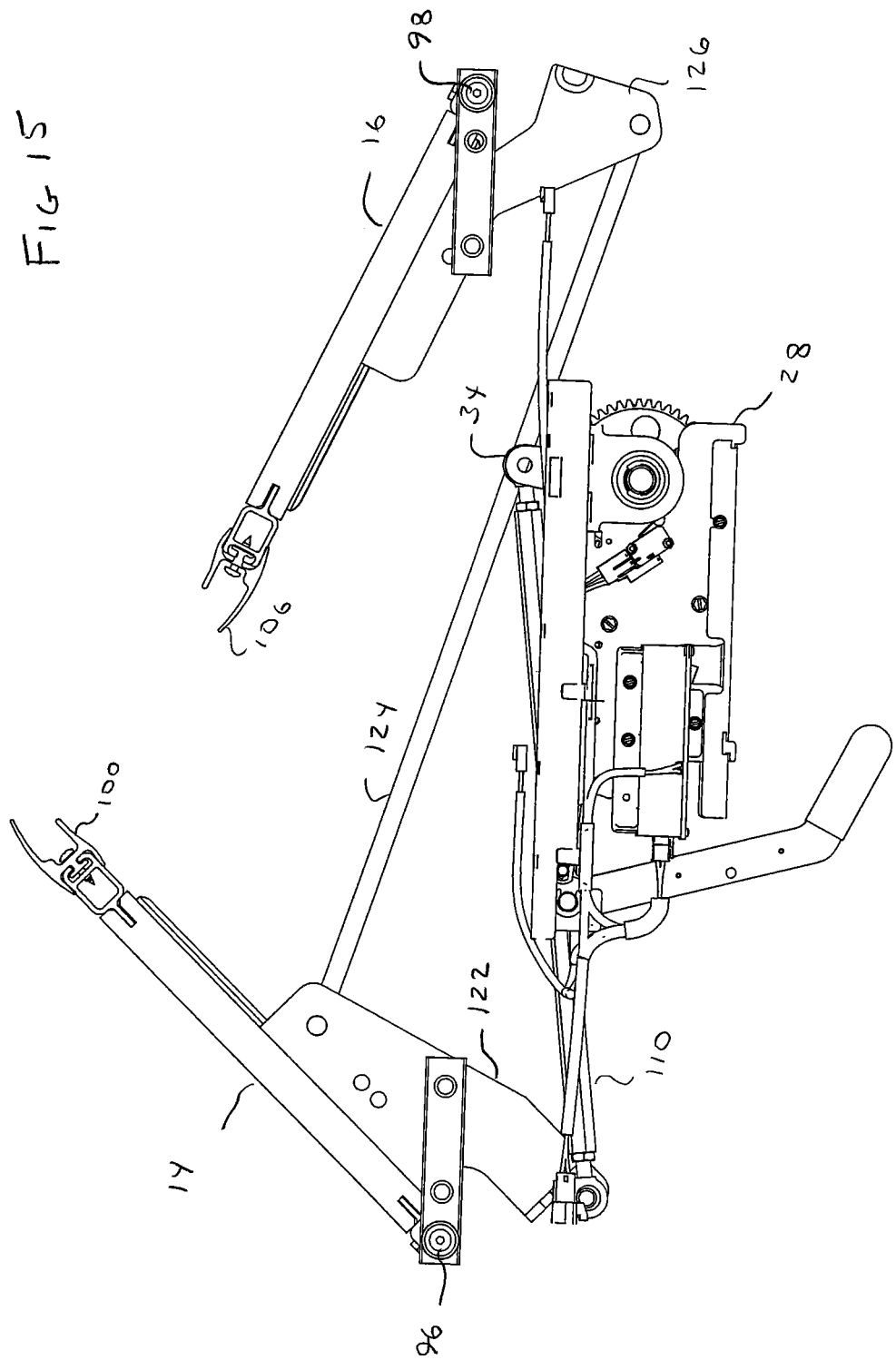
FIG. 15 is a top view of the actuator and the doors in partially open positions.
Figure 16:
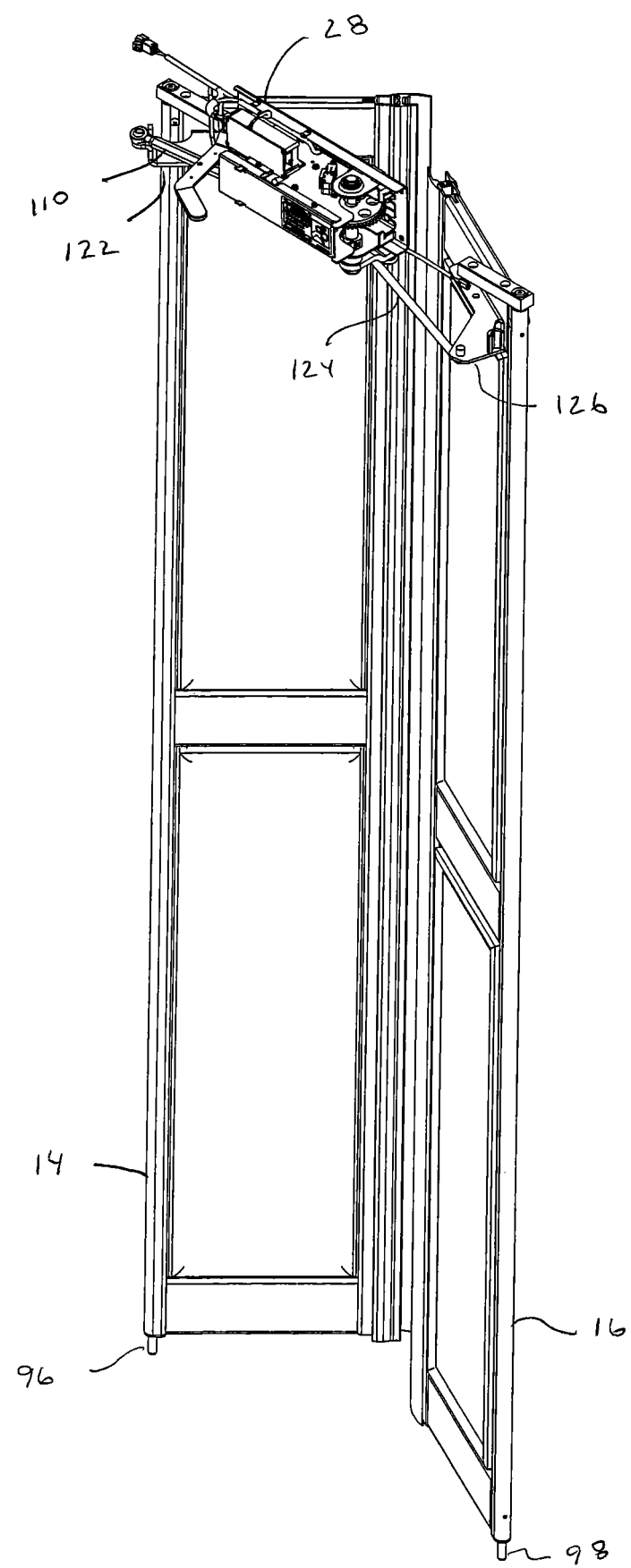
FIG. 16 is a back top right perspective view of the actuator and the doors in the partially open positions.
Figure 17:
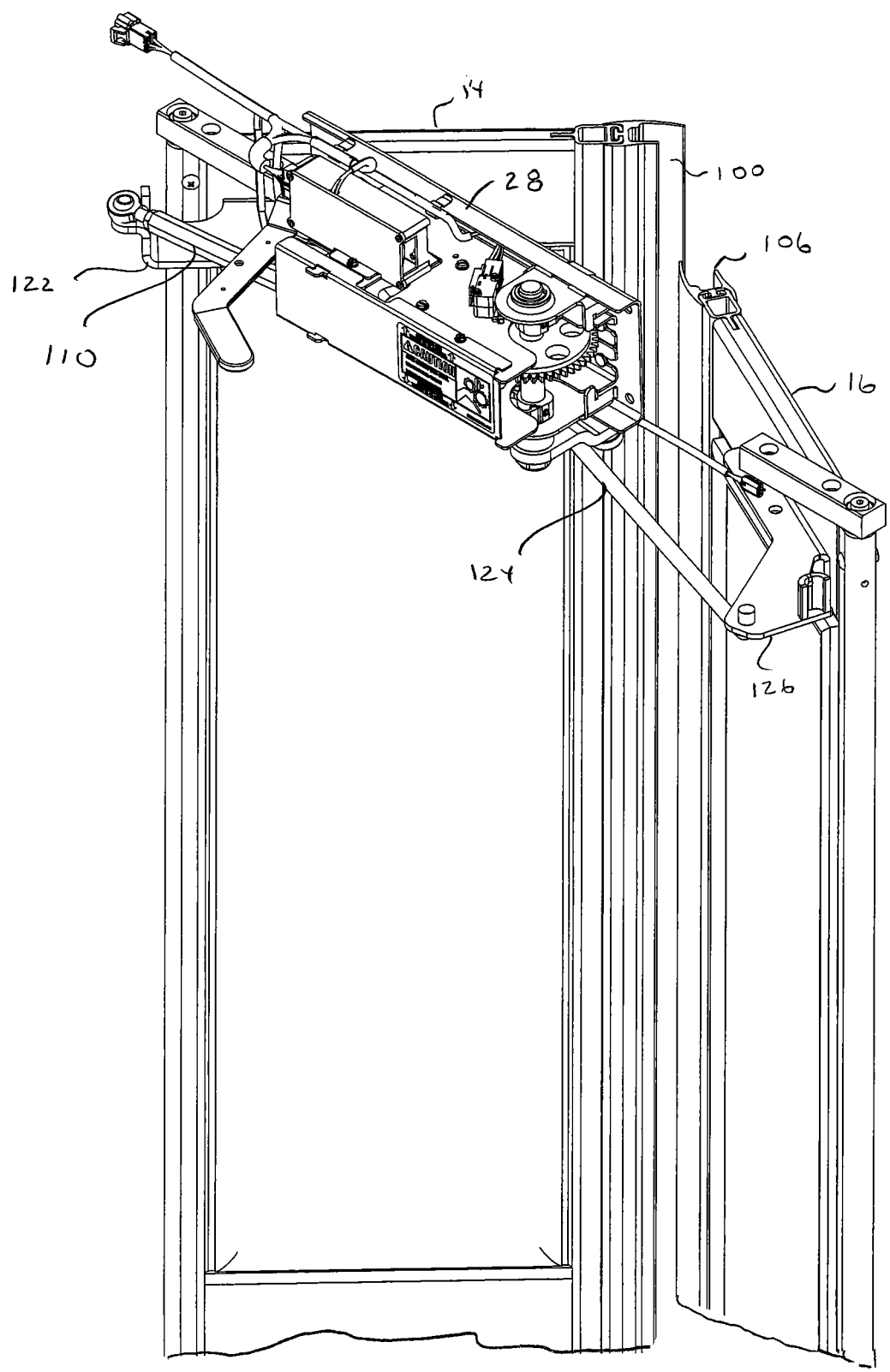
FIG. 17 is a back top right perspective view showing the actuator and upper portions of the doors in the partially open positions.
Figure 18:
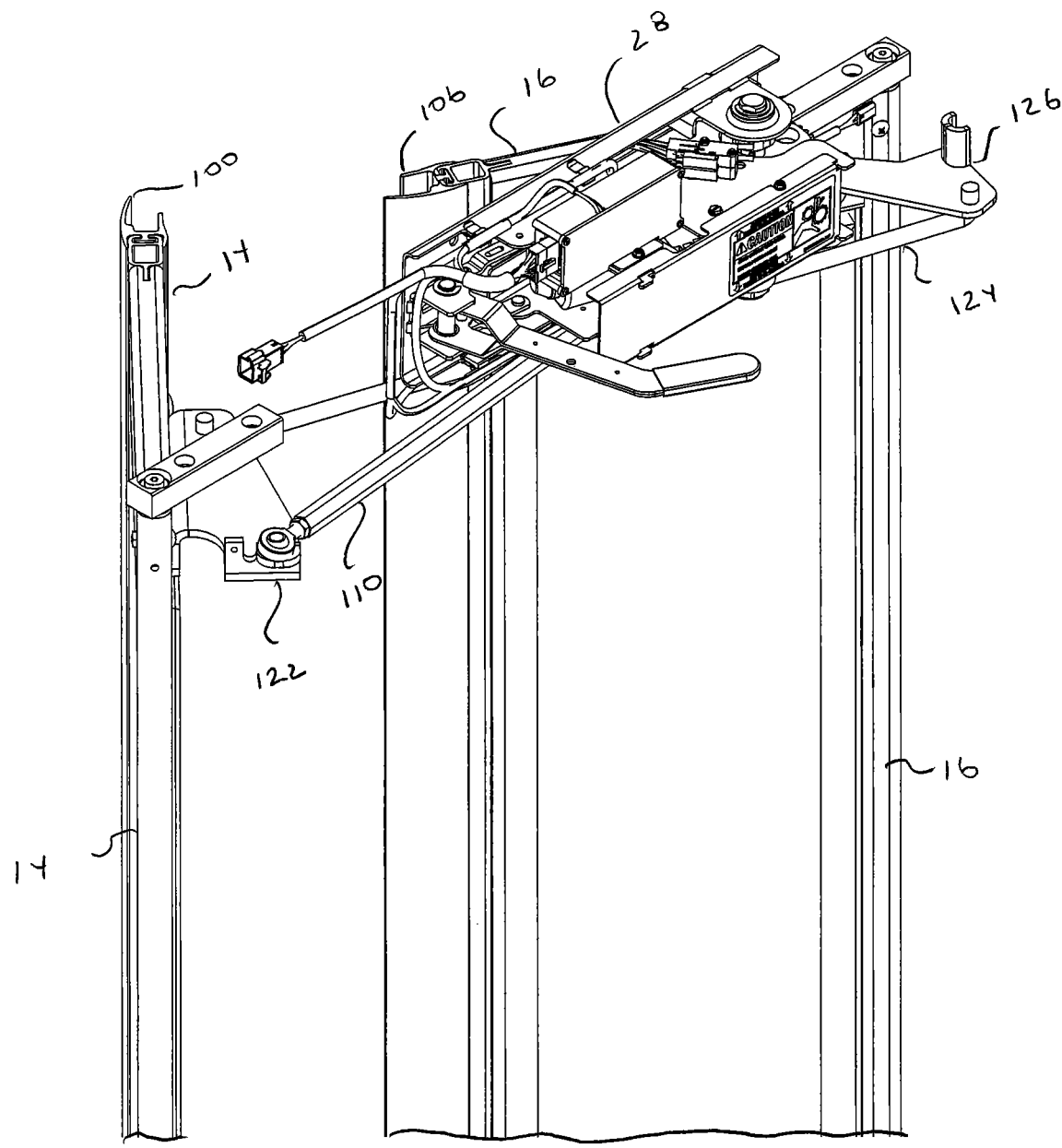
FIG. 18 is a back top left perspective view showing the actuator and upper portions of the doors in the partially open positions.
Figure 19:
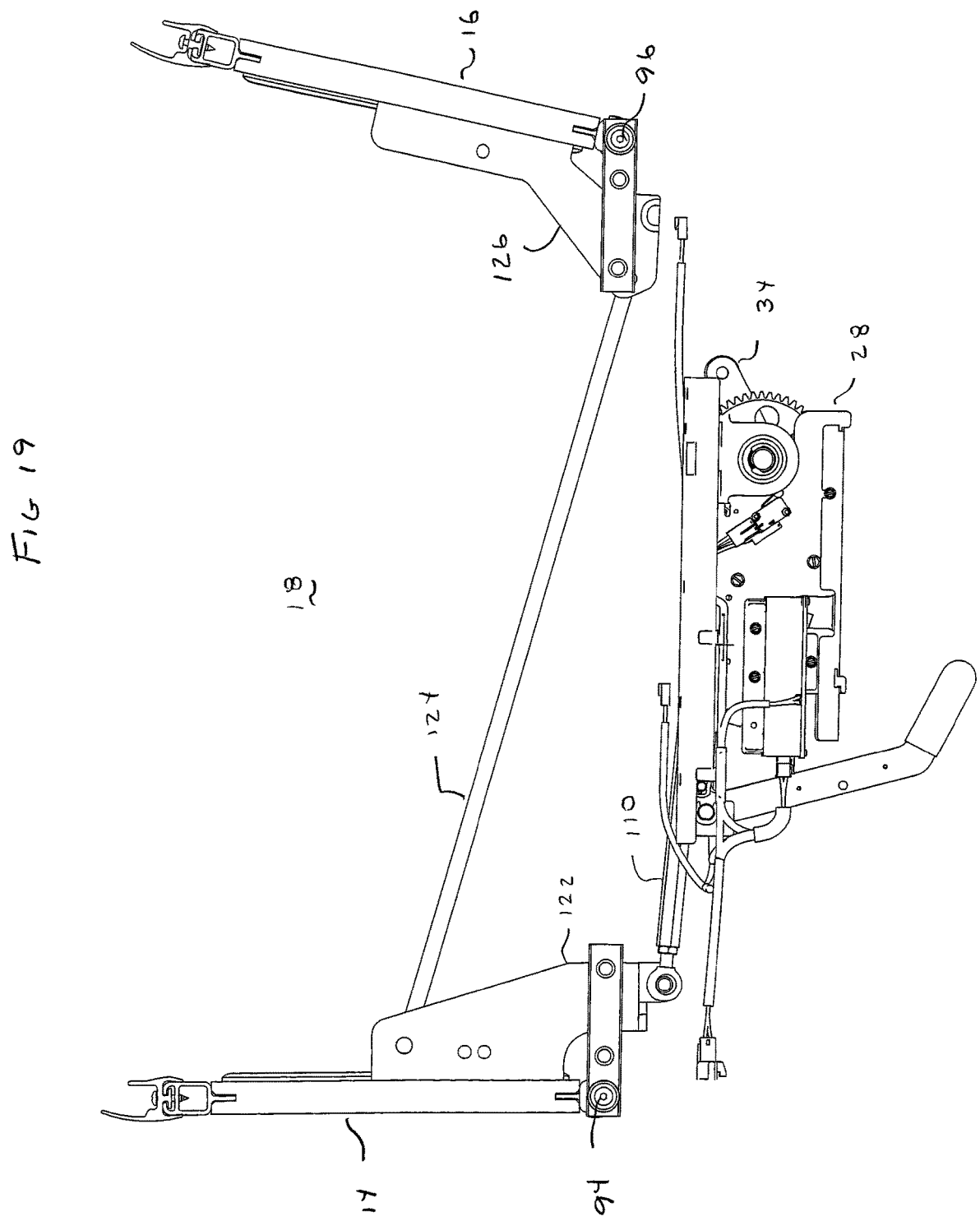
FIG. 19 is a top view of the actuator and the doors in the door open positions.
Figure 20:
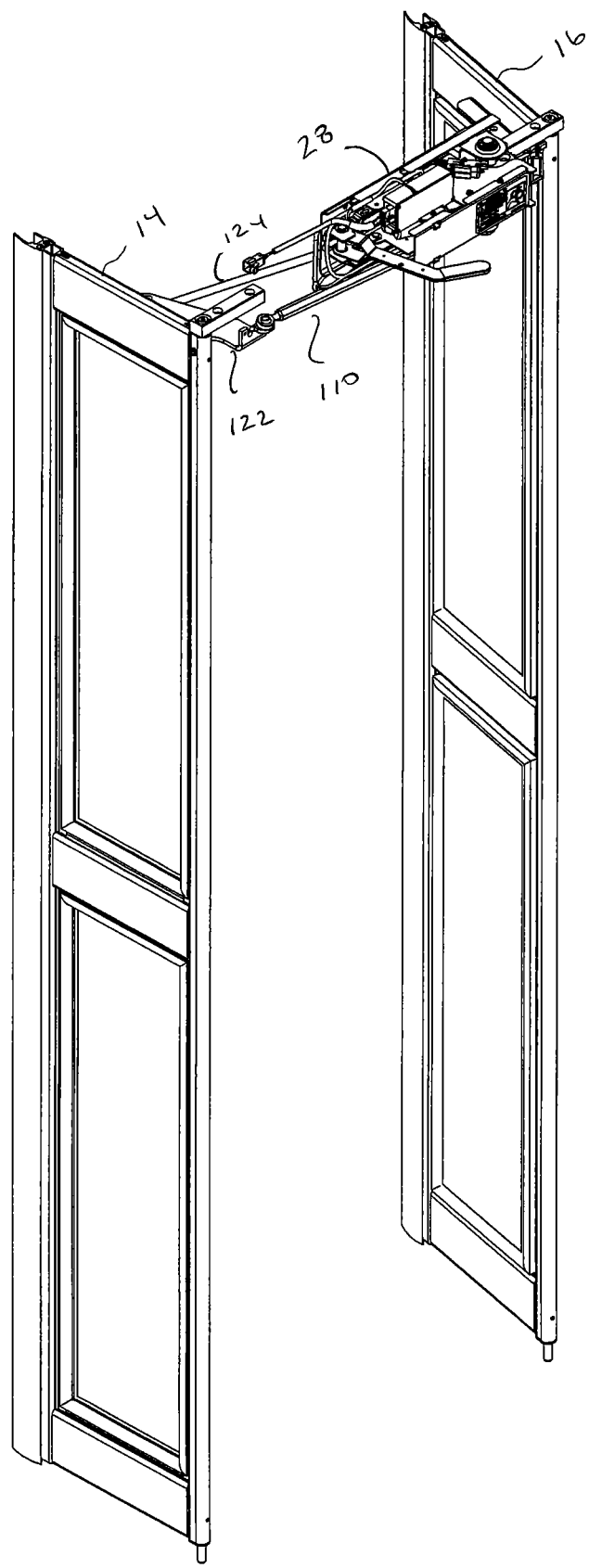
FIG. 20 is a back top left perspective view of the actuator and the doors in the door open positions.
Figure 21:
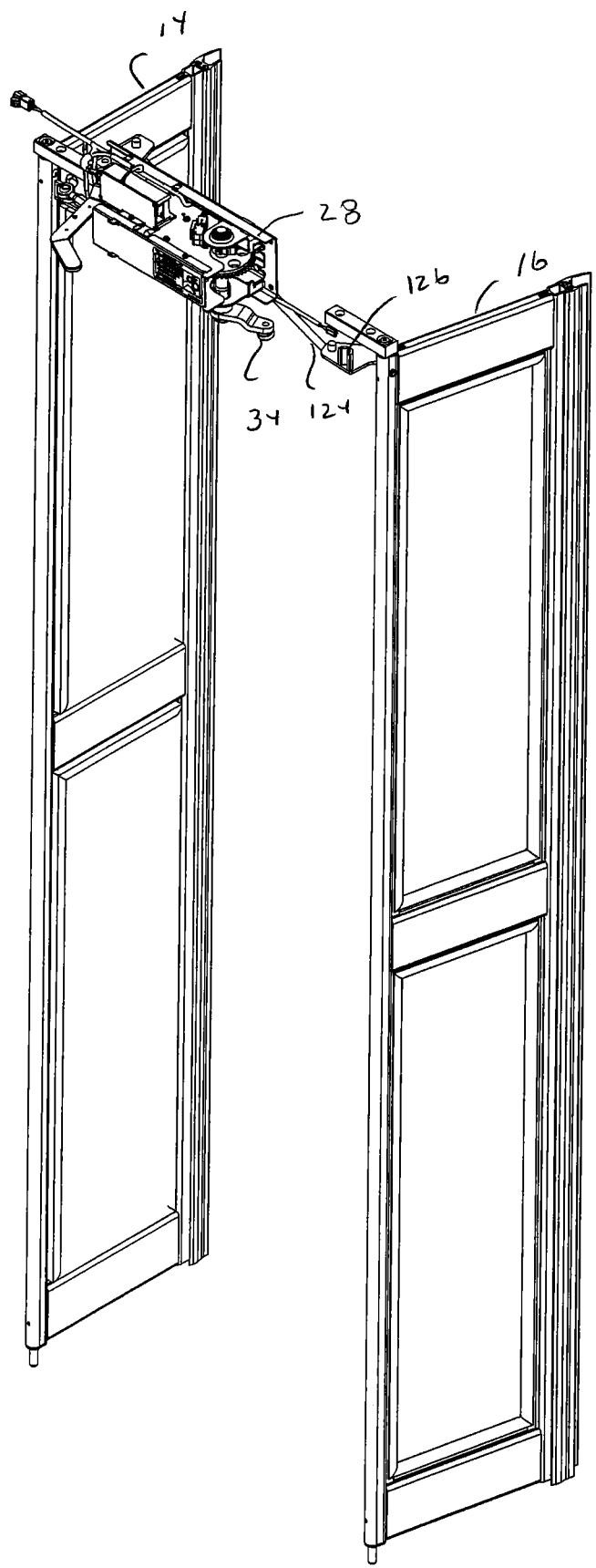
FIG. 21 is a back top right perspective view of the actuator and the doors in the door open positions.
Figure 22:
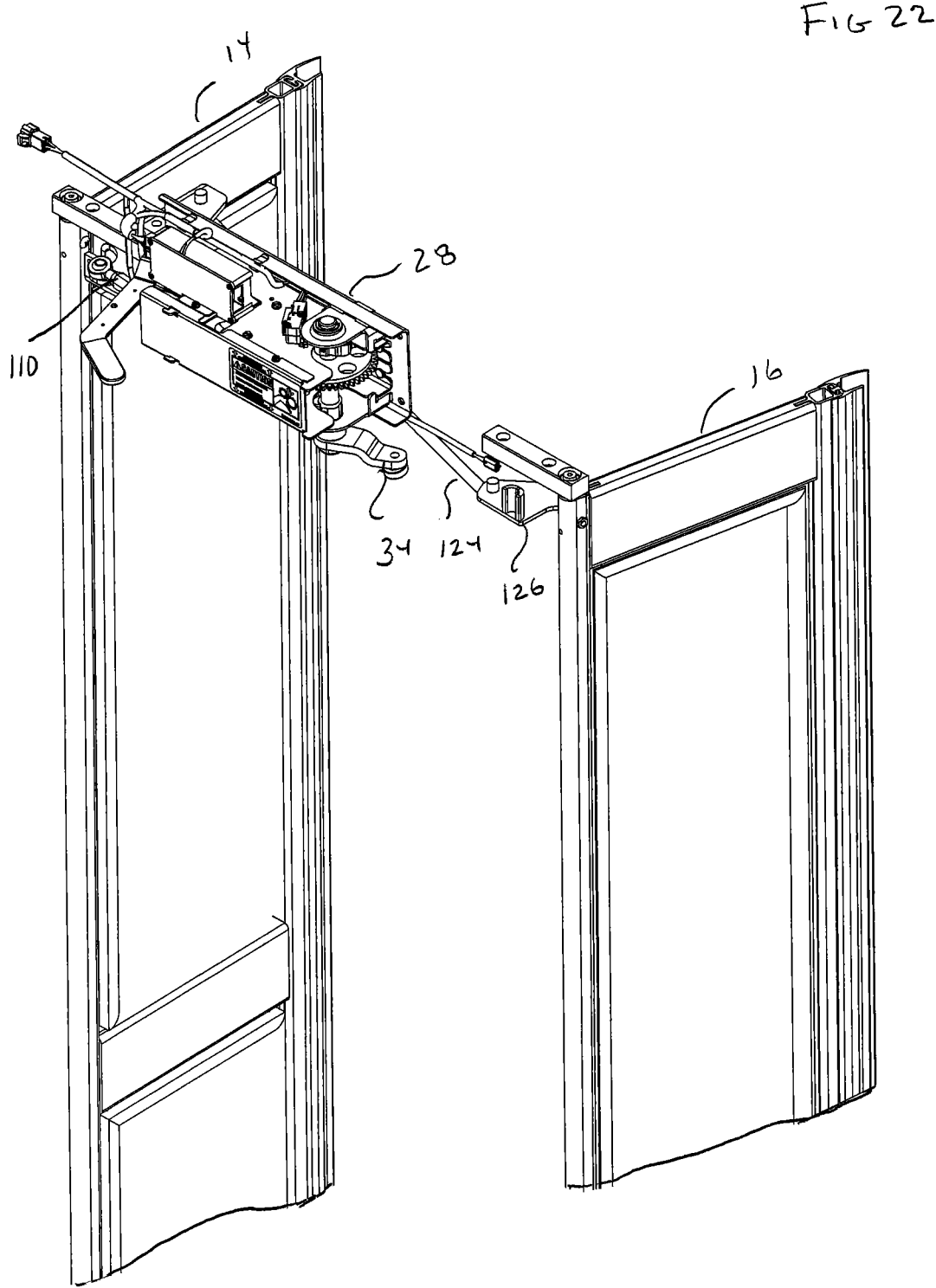
FIG. 22 is a back top right perspective view of the actuator and the upper portions of the doors in the door open positions.
Figure 23:
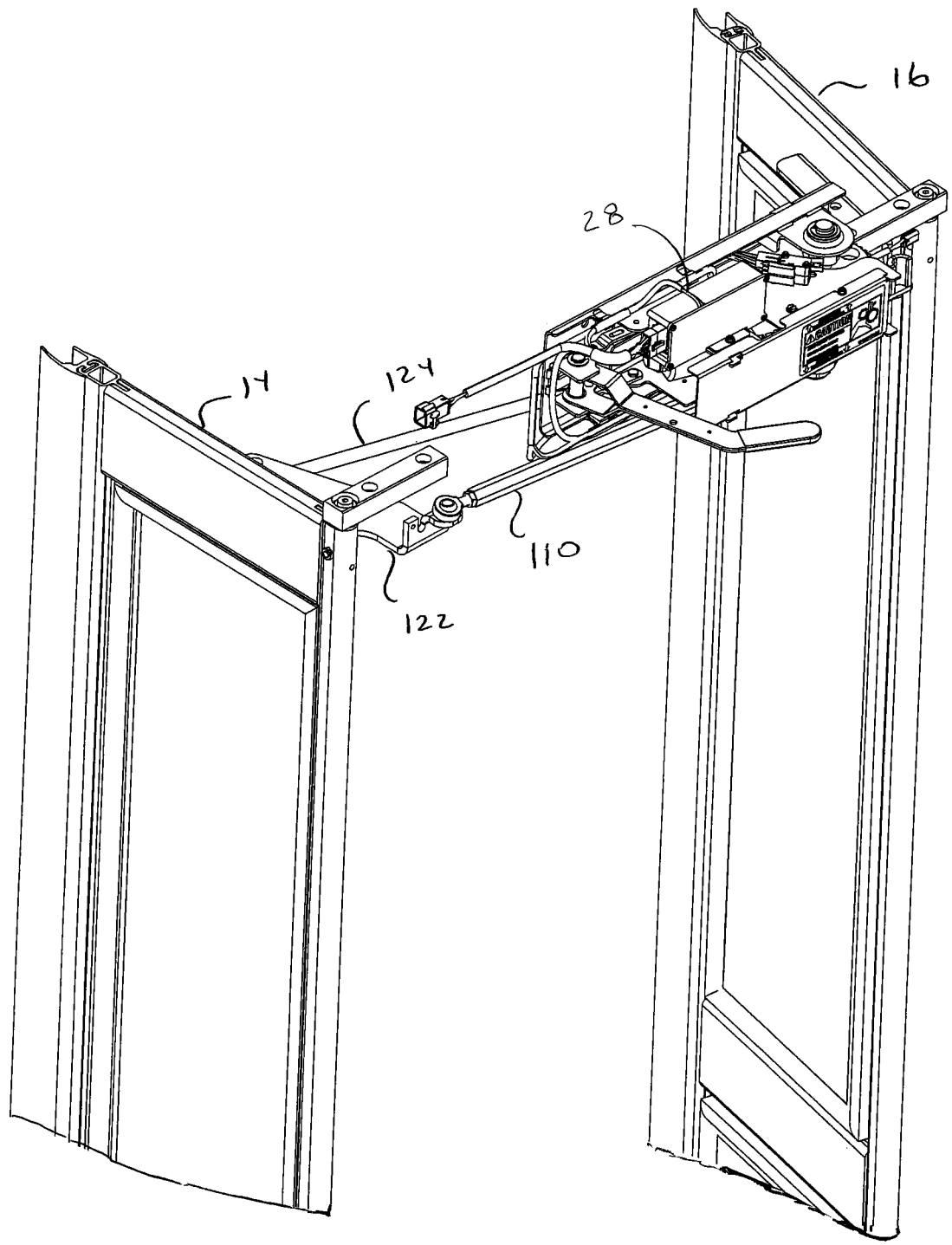
FIG. 23 is a back top left perspective view of the actuator and the upper portions of the doors in the door open positions.
Figure 24:
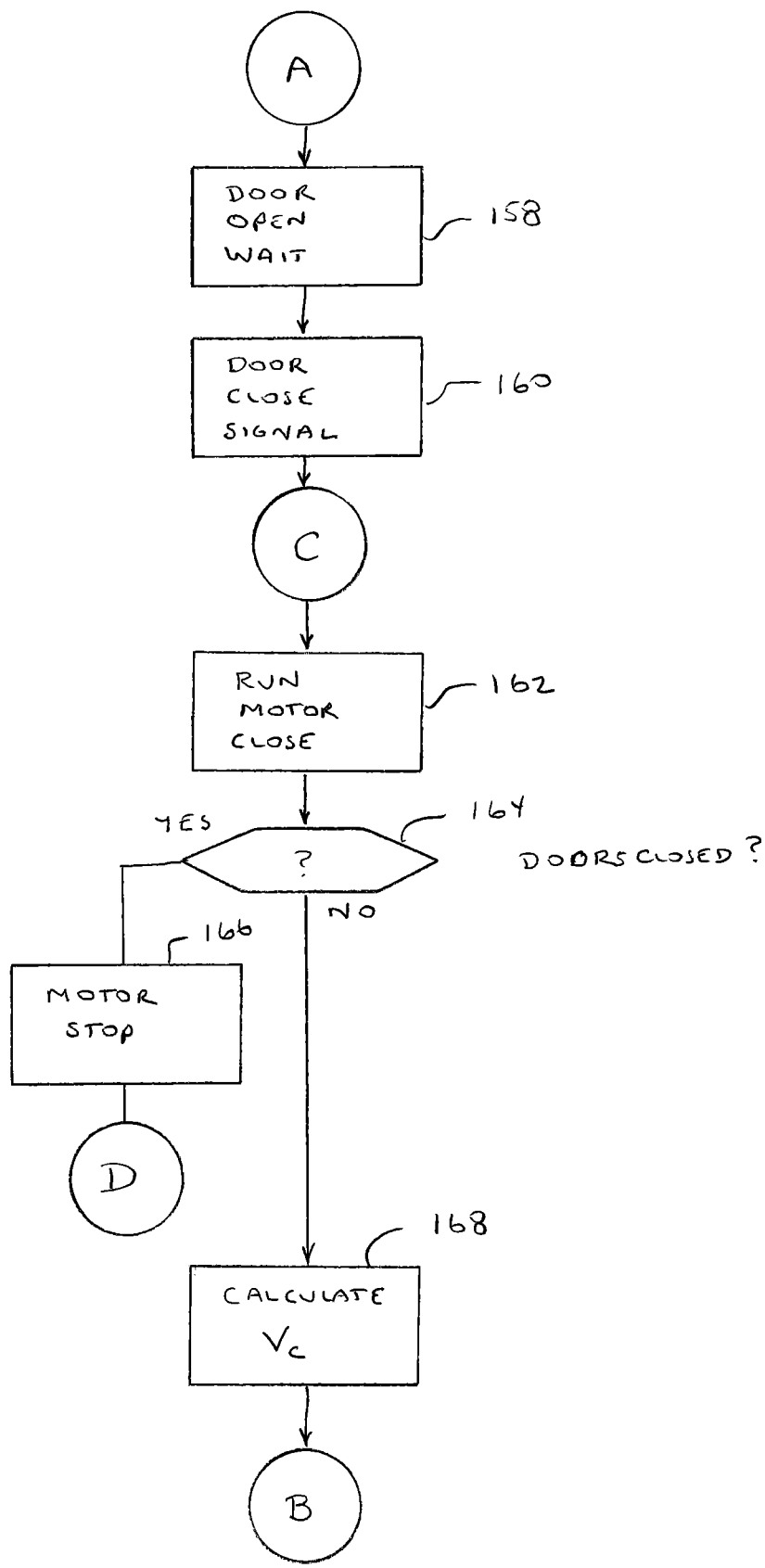
FIGS. 24-28 are schematic representations of control logic carried out by an exemplary controller that controls operation of the actuator which moves the doors between the open positions and the closed positions.
Figure 25:
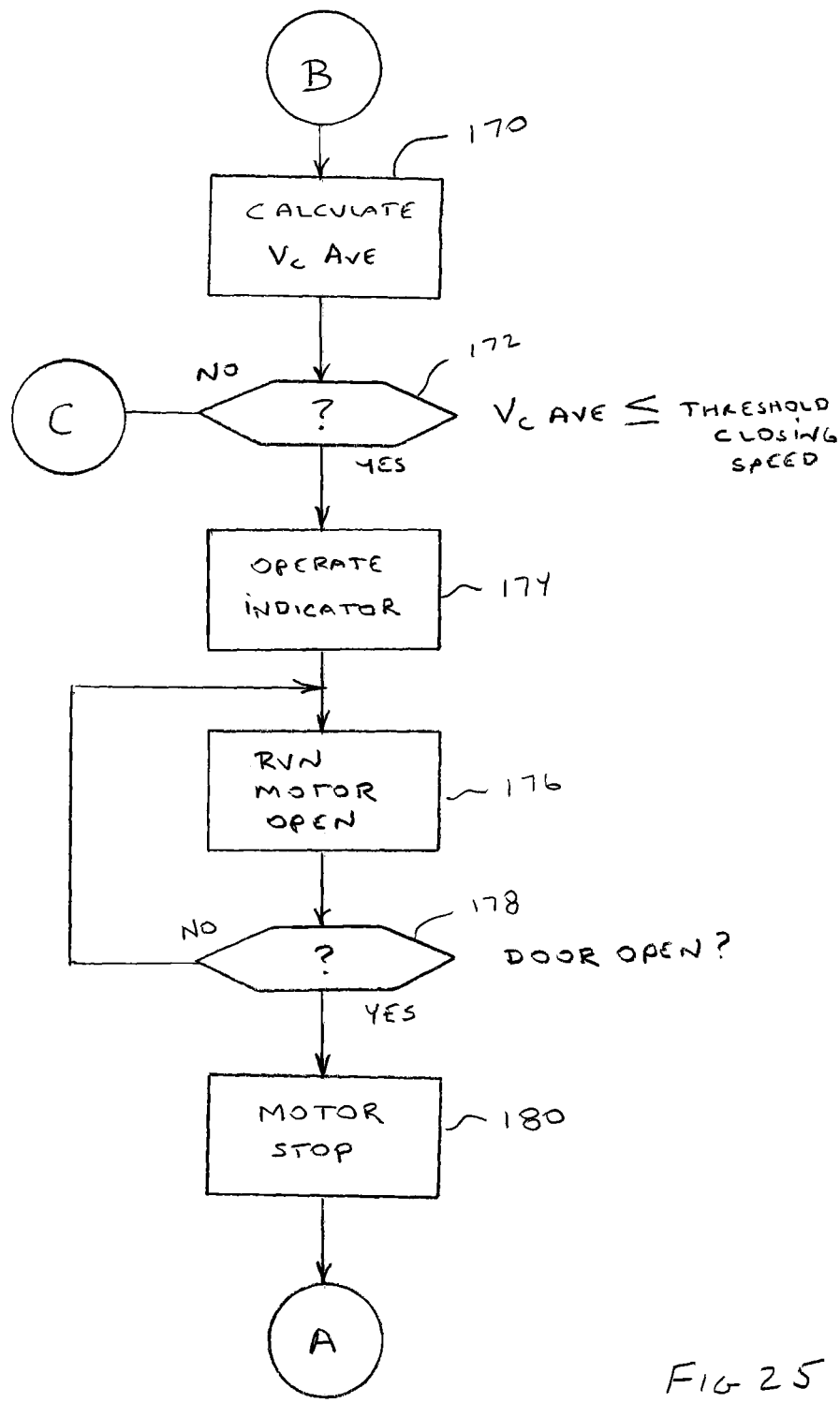
Figure 26:
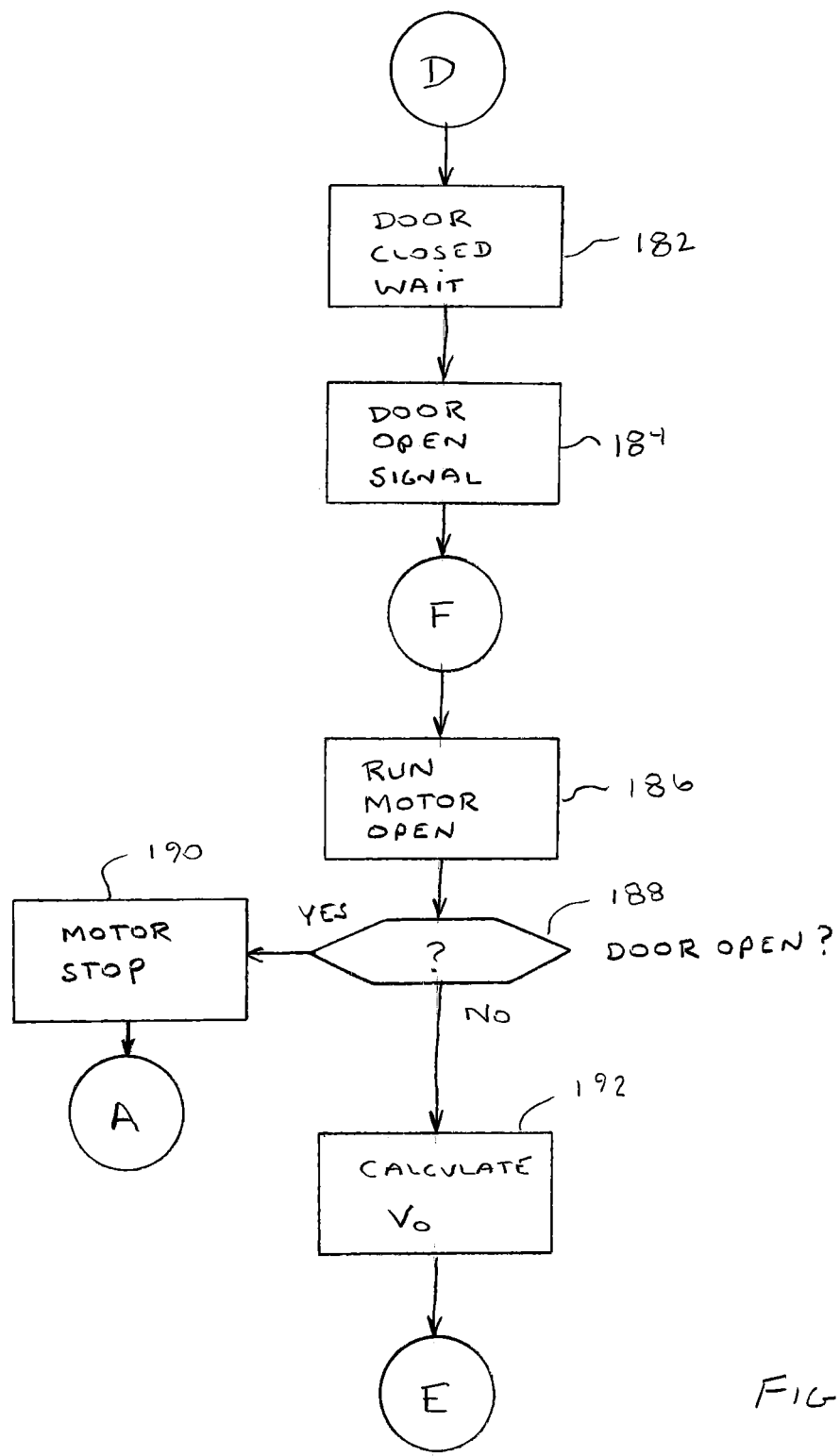
Figure 27:
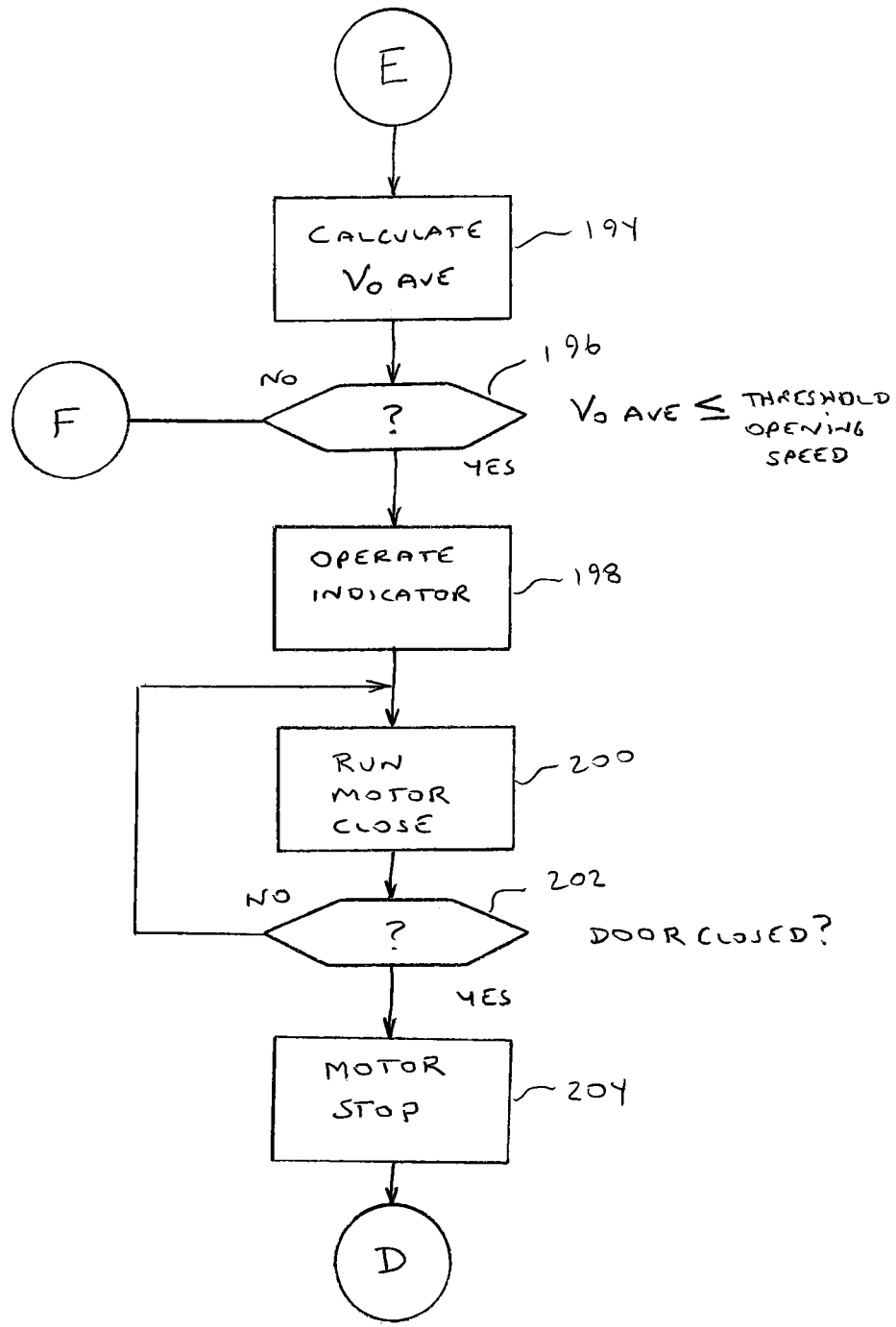

Movement of the drive lever 34 from the rotational position corresponding to the closed position of the doors in a rotational direction which is clockwise when viewed from the top of the actuator 28, causes the drive link 110 to move toward door 16. As shown in FIG. 15 such movement of the drive link 110 causes movement of the bracket 122 that is attached to door 14 which causes door 14 to rotate about axis 96 in a counterclockwise direction when viewed from above. The movement of bracket 122 causes the connecting rod 124 to move rotationally outward and to pull bracket 126 closer to door 14. This causes door 16 to rotate in a clockwise direction about axis 98 when viewed from the top. As a result the doors 14 and 16 begin to rotate about the respective axes to a partially open position as represented in FIGS. 15-18. As can be appreciated the rotation of the drive lever 34 causes the doors to move in coordinated relation together from the door closed positions toward the door open positions.

Further movement of the drive lever 34 in the clockwise rotational direction when viewed from above the actuator 28, causes the doors 14, 16 to move to the fully open positions shown in FIGS. 19-23. In this position the drive link causes bracket 122 to rotate so that door 14 extends perpendicular to the direction the door 14 extends when in the door closed position. Connecting rod 124 causes bracket 126 and door 16 to be moved to a position in which the door 16 likewise extends perpendicular to the door 16 in the closed position. Likewise in this position doors 16 and 14 extend substantially parallel to one another. In this position the doors are disposed sufficiently horizontally from one another so that persons entering and leaving the bus can pass between the doors along the open path 18. Further in the exemplary arrangement with the doors in the door open positions, the lower cam switch 90 is operative to detect the contoured surface of the lower cam 48 to provide an indication that the drive lever is in a rotational position that corresponds to the fully open position of the doors.

As can be appreciated, from the door open positions shown in FIGS. 19-23, the doors 14, 16 may be returned to the door closed positions by operating the motor 82 to cause the drive lever 34 to rotate in an opposed rotational direction from that in which the drive lever rotates to open the doors. Thus doors 14 and 16 are caused to be moved together in coordinated relation between the respective door closed positions and door open positions responsive to the actuator. However it should be understood that the actuator and the linkages used for connecting the actuator and the doors is exemplary and in other arrangements other approaches may be used.

Figure 9:
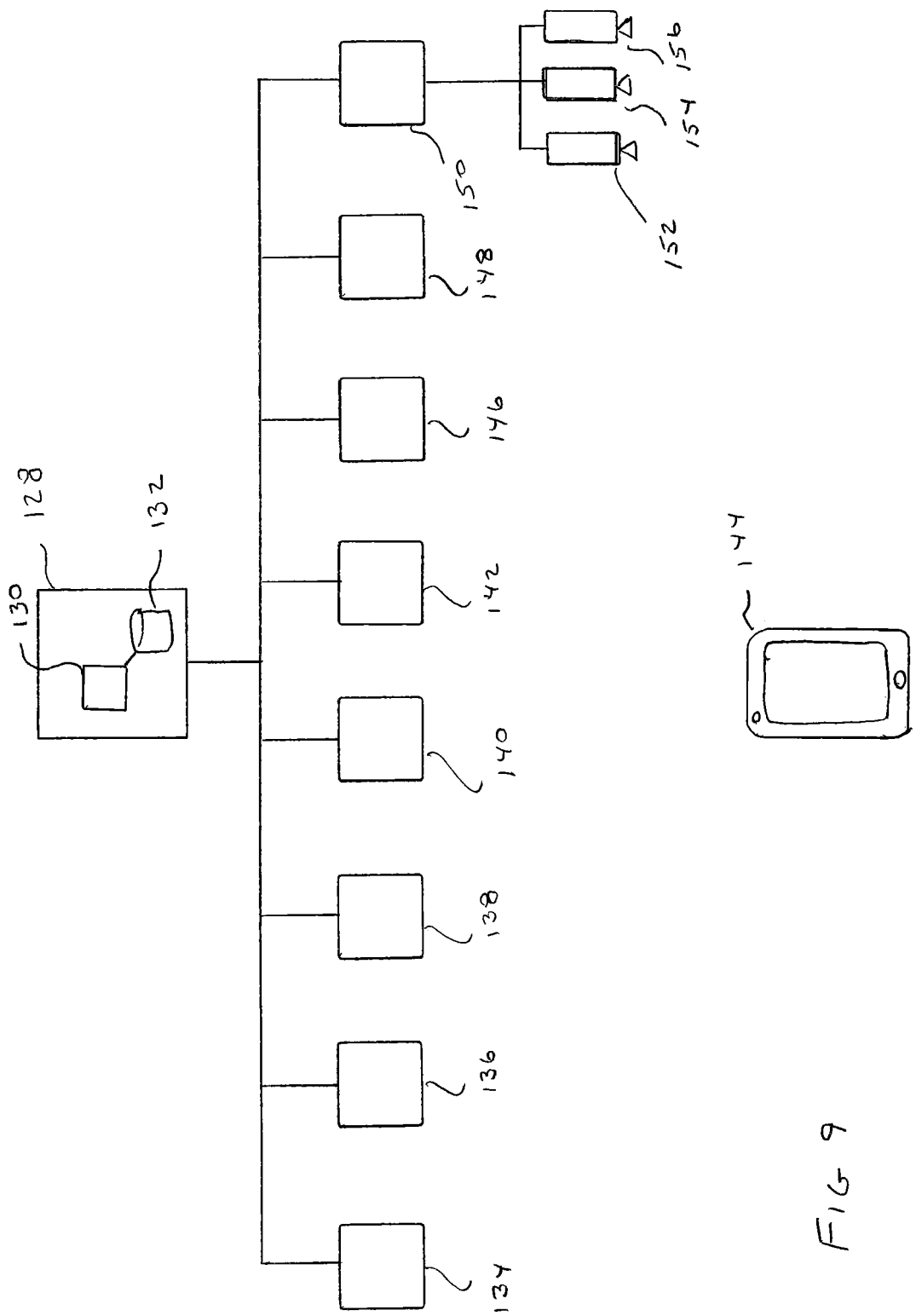
FIG. 9 is a schematic view of control circuitry associated with the exemplary door control apparatus.

In the exemplary arrangement the actuator 28 is in operative connection with at least one controller 128. The at least one controller which is shown schematically in FIG. 9 includes one or more circuits which are operative to communicate electrical signals which can control the operation of the motor 82 and other devices which are in operative connection therewith. In the exemplary arrangement the at least one controller 128 includes at least one circuit including a processor schematically indicated 130 and at least one data store schematically indicated 132. In exemplary arrangements the processor may include a processor suitable for carrying out circuit executable instructions that are stored in the one or more associated data stores. The processor includes or is in connection with a nonvolatile storage medium including non-transitory circuit executable instructions that may include a basic input/output system (BIOS). For example, the processor may correspond to one or more or a combination of a CPU, FPGA, ASIC or other integrated circuit or other type of circuit that is capable of processing data and instructions. The data stores may correspond to one or more of volatile or nonvolatile memories such as random access memory, flash memory, magnetic memory, optical memory, solid-state memory or other devices that are operative to store circuit executable instructions and data. Processor executable instructions may include instructions in any of a plurality of programming languages and formats including, without limitation, routines, subroutines, programs, threads of execution, objects, scripts, methodologies and functions which carry out the actions such as those described herein. Structures for processors may include, correspond to and/or utilize the principles described in the textbook entitled Microprocessor Architecture, Programming and Applications with the 8085 by Ramesh S. Gaonker (Prentice Hall 2002) which is incorporated herein by reference in its entirety.

The exemplary data stores used in connection with exemplary arrangements may include any one or more of several types of mediums for holding circuit executable instructions and/or data. These may include, for example, magnetic media, optical media, solid-state media or other types of media such as RAM, ROM, PROMs, flash memory computer hard drives or any other form of media suitable for holding data and circuit executable instructions. Exemplary controllers may further include other components such as hardware and/or software interfaces for communication with the devices and systems in which they are connected.

In the exemplary arrangement the at least one controller 120 is in operative connection with at least one sensor 134. In the exemplary arrangement the at least one sensor is in operative connection with the drive lever 34 and is operative to sense data that is usable to determine the rotational position of the drive lever. In an exemplary arrangement the at least one sensor 134 may correspond to the upper cam switch 88 and upper cam 46 and the lower cam switch 90 and the lower cam 48. In other exemplary arrangements the at least one sensor 134 may include a potentiometer, an optical encoder, a Hall Effect sensor, and inductance sensor, a magnetic sensor or other suitable sensor for detecting features or properties usable to determine a rotational position of the drive lever.

In the exemplary arrangement the controller 128 is in operative connection with an audible annunciator 136. The audible annunciator 136 is selectively operative responsive to signals from the controller to provide an audible signal. Such an audible signal may be usable to provide a warning or other indication in a manner like that hereafter discussed. The exemplary controller 128 is further in operative connection with a visual indicator 138. The exemplary visual indicator 138 is operative to provide a visual indication of the condition detected by the controller that may be indicative of a problem or potential problem associated with the operation of the doors or other components of the system.

At least one manually actuatable switch 140 is also in operative connection with the controller 128. In the exemplary arrangement the at least one manually actuatable switch 140 is located in the interior area of the bus. Manual actuation of the switch 140 by the bus driver or other authorized operator is used in the exemplary arrangement to cause the actuator to operate to rotate the drive lever to move the doors between the door open and door closed positions.

In the exemplary arrangement the controller 128 is in operative connection with a wireless portal 142. The exemplary wireless portal 142 comprises a transceiver that is operative to enable wireless communication between the controller 128 and at least one user mobile device 144. The wireless communication portal may include a suitable chipset or other suitable circuitry. The exemplary user mobile device may be operated by an authorized user such as the bus driver, to monitor information about the bus and to control certain aspects of the bus when the bus driver is outside the bus. In an exemplary arrangement the user mobile device includes a processor circuit of the type previously discussed and at least one data store which is usable to hold circuit executable instructions. The exemplary mobile device further includes input and output devices such as a touchscreen interface, input devices such as a camera, buttons and/or microphone and output devices such as a speaker and a display. Of course these input and output devices are exemplary and other arrangements other devices may be used. The exemplary user mobile device further includes a wireless communication chipset or other wireless communication circuitry that enables the user mobile device to communicate with the controller 128 through the wireless communication portal 142. In some exemplary arrangements the user mobile device may include a dedicated device for use in connection with the controller 128 and the bus with which the controller is associated. In other exemplary arrangements the user mobile device may include a smart phone, tablet or other computer device operated by the user that includes circuit executable instructions for performing the capabilities described herein.

The exemplary system further includes a motion sensor 146. In the exemplary arrangement the motion sensor 146 is operative to determine if the bus is currently in motion. The exemplary system further includes a contamination sensor 148. In the exemplary arrangement the contamination sensor 148 includes at least one of a smoke sensor, carbon monoxide sensor or carbon dioxide sensor or other sensor that is operative to detect a dangerous level of a contaminant within the interior area of the bus.

Figure 10:
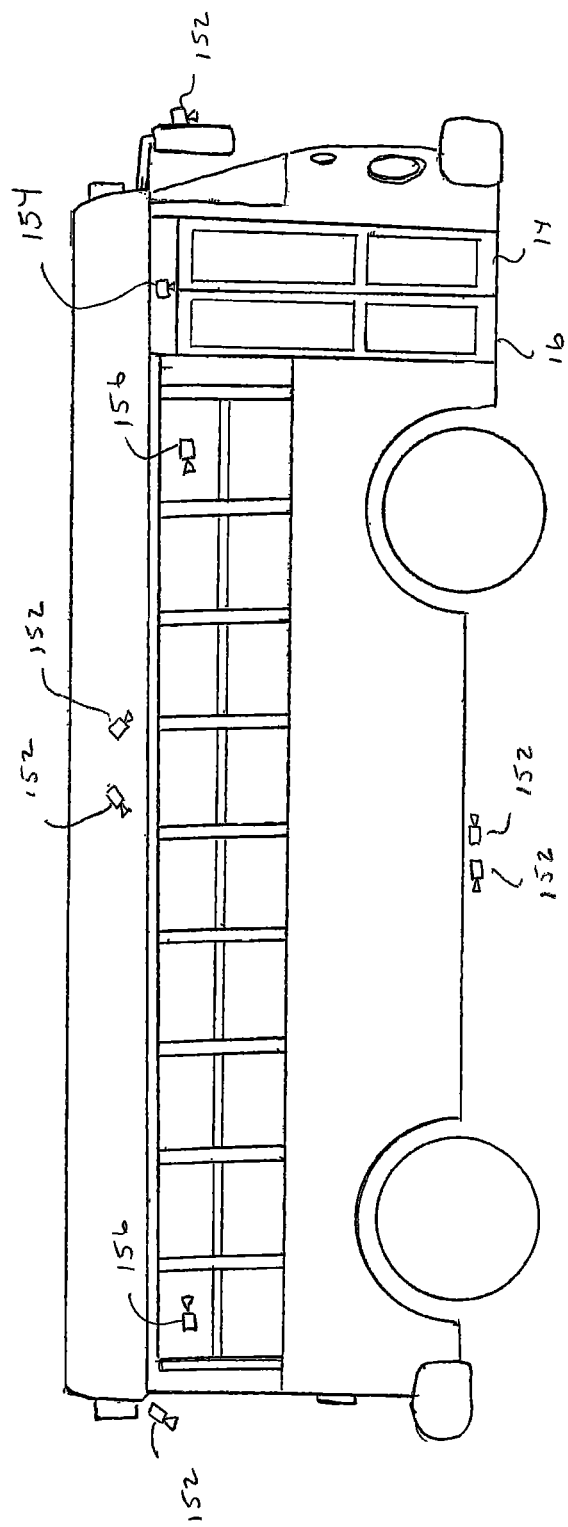
FIG. 10 is a schematic view showing an exemplary bus with a plurality of cameras or other image capture devices.

Further in the exemplary arrangement the controller 128 is in operative connection with a camera interface 150. The exemplary camera interface is in operative connection with a plurality of cameras that are operative to capture images within the interior area of the bus or in proximity thereto. For example, in an exemplary arrangement at least one external area camera has a field of view that includes a portion of the exterior area 20 of the bus. As schematically represented in FIG. 10 exterior area cameras 152 may have a field of view that includes areas adjacent to a front and a rear of the bus as well as along the sides of the bus. Other exterior area cameras 152 may have a field of view that includes other external areas such as underneath the bus or other locations where passengers or unauthorized individuals may be located.

The exemplary system further includes at least one entry area camera 154. The at least one entry area camera 154 includes a field of view of the entry area 22 adjacent to the doors 14 and 16. In exemplary arrangements entry area cameras 154 may be located to have a field of view either externally of the bus in the entry area or in the bus interior area in the entry area adjacent to the doors, or in both locations.

Further the exemplary system further includes at least one interior area camera 156. The at least one interior area camera 156 has a field of view that includes the interior area 12 of the bus. In some exemplary arrangements at least some of the cameras may provide night vision image capture capabilities and/or image element temperature detection. Such cameras may be capable of detecting the presence of persons, animals or other objects in darkness or near darkness conditions. Of course it should be understood that these cameras are exemplary and in other arrangements other or additional cameras may be used. Likewise it should be understood that the devices that are shown in operative connection with the at least one controller 128 are merely examples of the types of devices that may be included in such a system. Other devices may be included in alternative systems for purposes of detecting conditions and for providing information that may be useful to the driver or in the operation of the bus.

FIGS. 24-28 schematically describe the logic flow carried out by the at least one controller 128 in opening and closing the doors 14, 16. In the exemplary arrangement the at least one data store 132 includes data corresponding to a threshold closing speed. The threshold closing speed corresponds to an acceptable speed at which the drive lever rotates when moving the doors between the door open positions and the door closed positions. In the exemplary arrangement the at least one data store 132 further includes data corresponding to a threshold opening speed. The threshold opening speed corresponds to an acceptable speed at which the drive lever rotates when moving the doors between the door closed positions in the door open positions. In some exemplary arrangements both the threshold closing speed and the threshold opening speed may be a common value.

In the exemplary arrangement with the doors in the door open positions the at least one controller 128 waits to receive a signal from the at least one manually actuatable switch 140 indicating that the driver of the bus or other operator wishes to close the doors. This wait state is reflected in FIG. 24 by a step 158. Step 160 represents receipt by the at least one controller of the signal from the at least one manually actuatable switch 140 corresponding to an input to move the doors to the closed positions. Responsive at least in part to receipt of the door close signal, the at least one controller 128 operates to cause the motor 82 of the actuator 28 to run so that the drive lever 34 moves in a rotational direction which causes the doors to move towards the closed positions. This is represented by a step 162.

The at least one controller then operates to continue to cause the motor to rotate the drive lever while sensing for a signal from the at least one lever position sensor 134 which indicates that the doors are in the door closed positions. This is represented by a step 164. If the drive lever reaches the rotational position corresponding to the doors being closed as determined in step 164, the controller operates to cause the motor 82 to stop operation. This is represented by a step 166.

If in step 164 the controller determines that the drive lever is not in a rotational position that corresponds to the doors being closed, the controller then operates to calculate a speed of the drive lever in its current rotational position. This is represented by a step 168. In the exemplary arrangement the controller then operates to calculate a closing speed value of the drive lever. This is represented by a step 170. In the exemplary arrangement the closing speed value is calculated as a function of the detected speed of the drive lever in each of a plurality of angularly disposed positions. In the example arrangement the closing speed value is calculated as an average of the most recent detected closing speed at the current rotational position of the drive lever, and a plurality of prior closing speeds calculated in previous rotational positions of the drive lever. This is done in the exemplary arrangement to calculate a closing speed that accurately represents the closing speed of the drive lever. Otherwise, in some arrangements if the closing speed calculation is based on speed detected at a single rotational position, such speed could be a speed value which is instantaneously or erroneously detected, and that is not representative of the actual closing speed. For example, if wear or other factors in the linkage which connects the drive lever to the doors causes an instantaneous slowing in rotational movement of the drive lever, this could be erroneously identified as the doors encountering an obstruction. Of course it should be understood that in other arrangements the approach of using an averaging process for purposes of determining the current closing speed may not be utilized. Likewise in other exemplary arrangements sensors may be utilized which detect the positions and speeds of components other than the drive lever for purposes of calculating the current closing speed.

As represented in a step 172 the exemplary controller operates to determine if the calculated closing speed is at or below the stored closing speed threshold value stored in the at least one data store. If the calculated closing speed value is not at or below the stored threshold, the controller continues to run the motor of the actuator to cause the drive lever to move the doors toward the door closed positions. However if in step 172 the calculated current closing speed in the rotational direction has fallen to a level at or below the stored threshold value, this indicates that at least one of the doors has encountered an obstruction, such as a person or an object. Responsive to making this determination, the controller is operative in a step 174 to provide an indication of the condition. For example in exemplary arrangements the controller may operate to cause the audible annunciator 136 and/or the visual indicator 138 to output an audible and/or visual signal to indicate that the door has encountered an obstruction. Of course it should be understood that in other arrangements the controller may operate to determine that the closing speed is above a threshold or within certain limits.

As represented in a step 176 the exemplary controller is further operative responsive to the determination that the current closing speed of the drive lever is at or below the threshold closing speed, to cause the motor 82 to operate in an opposed rotational direction from that in which the motor operates to cause the doors to move toward the closed positions. The exemplary controller operates to cause the motor to operate to cease moving the doors toward the closed positions and to begin movement of the doors toward the open positions. This causes the doors to move away from the encountered obstruction. Thus for example if the doors have encountered the body of a passenger, the doors quickly disengage from the passenger. Of course it should be understood that this approach is exemplary and in other arrangements the controller may simply stop moving the doors towards the door closed positions, rather than cause the motor to reverse direction.

After the controller has caused the doors to reverse direction in the step 176, the exemplary controller then operates to determine if the doors have returned to the door open positions. This is done based on the rotational position of the drive lever as detected by the at least one sensor 134. If as represented by step 178, the at least one sensor 134 does not detect the drive lever in a rotational position corresponding to the door open positions, the controller continues to operate the motor 82 to move the doors toward the open positions. Once the at least one sensor 134 detects that the drive lever is in a rotational position corresponding to the doors being open, the at least one controller 128 operates to cause the motor 82 to stop operation. This is represented in a step 180. In the exemplary arrangement from the step 180, the bus driver can then take appropriate action to be sure that the entry area 22 is clear of obstructions, and then may again provide an input to the at least one manually actuatable switch 140 to cause the controller to move the doors toward the closed positions. Of course it should be understood that this approach is exemplary and in other arrangements other approaches may be used.

If the drive lever is rotated to a position in which the doors are in the closed positions, the exemplary at least one controller 128 operates to wait for an input to the at least one manually actuatable switch 140 indicating that the bus driver or other operator wishes to move the doors from the door closed positions to the door open positions. This is represented by a step 182. The at least one controller receives at least one signal from the at least one switch 140 indicating that the bus driver or other operator wishes to cause the doors to be opened. This is represented by a step 184. Responsive to receipt of the at least one signal indicating that the bus driver requests that the doors be opened, the at least one controller operates in accordance with its programming to operate the motor 82 to rotate the drive lever from the current rotational position in which the doors are held in the closed positions, toward a rotational position in which the doors are in the door open positions. This is represented by step 186

The at least one controller 128 then operates the motor 82 to move the doors toward the open positions while sensing for signals from the at least one sensor 134 which indicate the rotational positions of the drive lever, and the doors connected thereto. If in a step 188 the at least one controller determines that the drive lever has moved to a rotational position in which the doors are in the door open positions, the controller operates to cause the motor to stop operation. This is represented by step 190. In this situation both doors are in the open positions, and the at least one controller waits to receive at least one signal from the manually actuatable switch 140 indicating that the bus driver wishes to return the doors to the door closed positions.

If however in step 188 the doors are determined not to have reached the door open positions, the at least one controller is operative responsive at least in part to signals from the at least one sensor 134 to calculate the opening speed of the drive lever in its current angular position. This is represented by step 192. The exemplary controller then operates in accordance with its programed instructions to calculate a current opening speed as represented in step 194. In the exemplary arrangement the controller is operative to calculate the current opening speed as a function of the speed of the drive lever in each of a plurality of angular positions. In exemplary arrangements the current opening speed is calculated as an average of a plurality of the current drive lever velocity and the velocities at a number of prior rotational positions of the drive lever. This is done in a manner similar to the calculation of the current closing speed previously discussed. This approach is used in an exemplary arrangement to avoid adverse effects of transient conditions or erroneous signals which may not accurately represent the opening speed of the drive lever. Of course in other arrangements other approaches may be used.

As represented in a step 196 the exemplary at least one controller is operative to compare the calculated current opening speed and the stored threshold opening speed value stored in the at least one data store 132. The at least one controller is operative to make a determination if the current opening speed value is at or below the stored threshold opening speed. If the current opening speed is not at or below the threshold opening speed value, the at least one controller continues to cause the motor to operate to move the drive lever in the rotational direction which causes the doors to move toward the open positions. In other arrangements the circuitry may operate to determine that the opening speed is above a threshold or between certain limits.

In the exemplary arrangement if the current opening speed is at or below the threshold opening speed, the condition is indicative that at least one door has encountered an obstruction in moving between the door closed position and the door open position. Responsive to this determination at least one controller is operative to provide at least one output indicative of the condition. Such an output may be provided through the audible annunciator 136, the visual indicator 138, or both. The giving of such an indication is represented by a step 198. The at least one controller further operates responsive at least in part to the determination to cause the motor to cease causing the drive lever to move the doors toward the open positions. In the exemplary arrangement, the controller operates to cause the motor to reverse direction and cause the drive lever to move in a rotational direction which causes the doors to move back toward the closed positions. This is represented by step 200.

The exemplary at least one controller 128 operates the motor 82 to move the drive lever 34 in a rotational direction which causes the doors to move toward the door closed positions. The at least one controller then operates to monitor for signals from the at least one sensor 134 which would indicate that the drive lever has moved to a rotational position corresponding to both of the doors being closed. As represented by a step 202, if the signals from the at least one sensor 134 do not correspond to the doors being in the closed positions, the controller continues to operate the motor to cause the doors to move toward the closed positions. However if in step 202 the at least one controller determines that the rotational position of the drive lever corresponds to the doors being closed, the controller operates to cause the motor to cease operation with the doors in the door closed positions. This is represented by step 204. In the exemplary arrangement the controller operates to wait with the doors in the door closed positions for further signals from the bus driver or other operator to again open the doors after the bus driver has cleared the obstruction that prevented the doors from opening. Of course it should be understood that this logic flow and associated approaches are exemplary and in other arrangements other approaches may be used.

Figure 28:
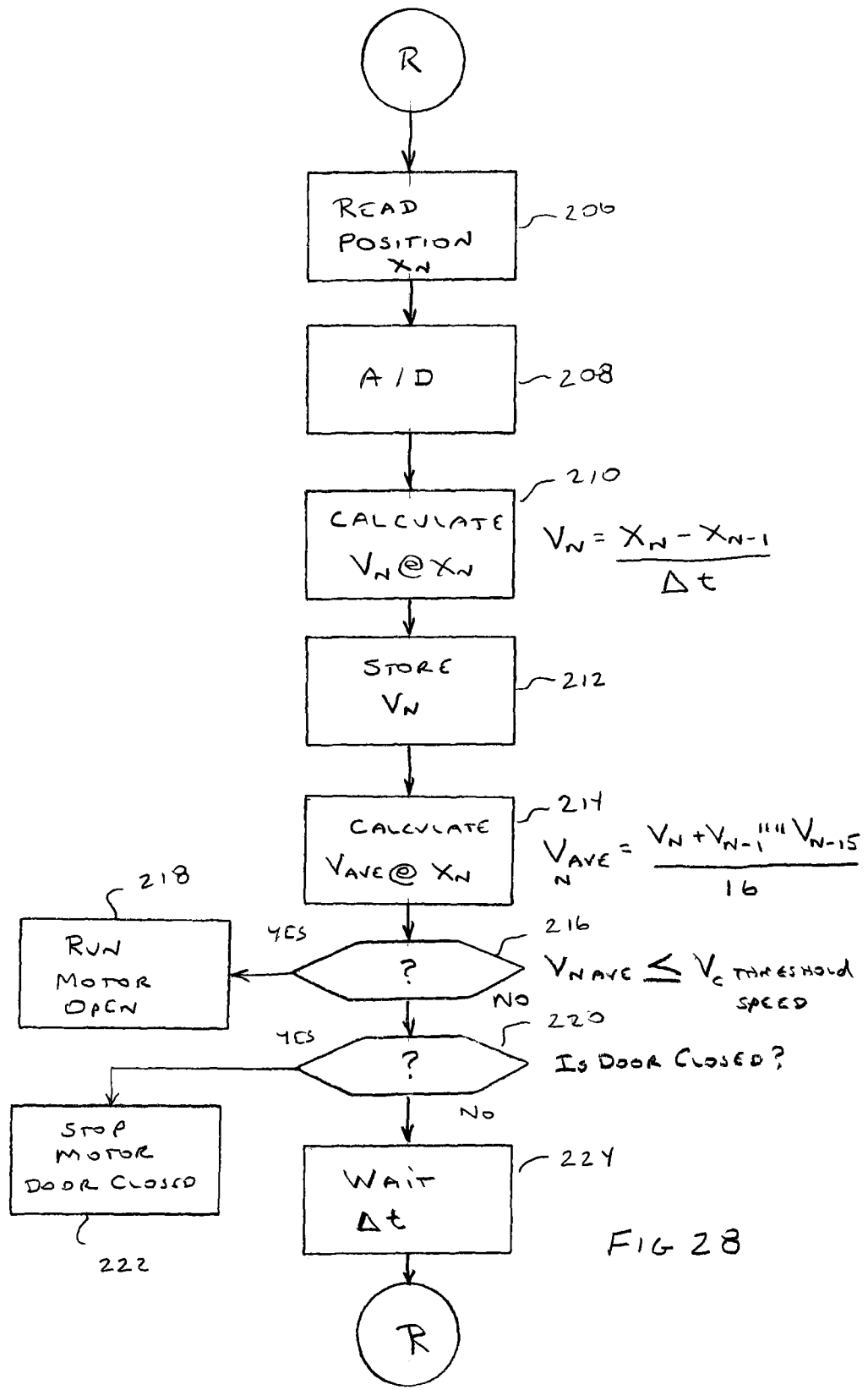

FIG. 28 discloses a schematic representation of an exemplary manner in which at least one controller may operate to determine the current closing speed value which is used for comparison with the stored threshold closing speed value for purposes of determining if one of the doors has encountered an obstruction. Of course it should be understood that similar logic may be utilized in connection with the calculation of the current opening speed value. It should further be understood that this logic flow is exemplary and in other arrangements other approaches to the calculation of the speed of the doors may be utilized for purposes of determining the presence of an obstruction.

In the exemplary arrangement the controller is operative to receive at least one signal from at least one sensor which is indicative of a rotational position of the drive lever. This is represented by step 206. In some exemplary arrangements the position signal may correspond to a voltage reading from a potentiometer, a signal from an encoder, a count signal from a position indicator, a value which indicates the position of a surface of the cam, or other suitable sensor signal from a sensor such as the at least one position sensor 134 of the types previously described. In the exemplary arrangement the circuitry associated with the controller is operative to convert an analog signal received from the at least one sensor to a digital signal. This is represented by step 208. Of course it should be understood that for some types of sensors the step of converting the signal from an analog signal to a digital signal may not be necessary.

In a step 210 the at least one controller is operative to calculate the velocity at the current rotational position of the drive lever. In the exemplary arrangement the velocity is calculated based on the difference in displacement of the drive lever at the current position at which the current reading is made, to the immediately preceding reading, divided by the difference in time between the readings. In exemplary arrangements the calculation is made for different readings during a very short time period. The controller next operates as indicated by step 212 to store the most recently calculated velocity value in the at least one data store 132.

In the exemplary arrangement the at least one controller 128 then operates to calculate the current closing speed as represented by step 214. In the exemplary arrangement the current closing speed is calculated as an average of the immediately preceding 16 instantaneous velocity values. Of course it should be understood that this approach is exemplary and in other arrangements other calculations and included values may be utilized for purposes of making a determination as to a current closing speed.

The at least one controller then operates as represented in a step 216 in a manner similar to that previously discussed, to make a determination if the current closing speed is at or below the threshold closing speed stored in the at least one data store. If the current closing speed is at or below the threshold it is considered indicative that the doors have encountered an obstruction, and the at least one controller operates in accordance with its executable instructions responsive to the determination to stop moving the doors toward the closed position and reverses the operation of the motor to move the doors toward the open positions. This is represented by step 218. If the current closing speed is calculated as above the threshold, the controller continues to operate the motor to move the doors toward the door closed positions until the at least one sensor 134 provides a signal to the controller to indicate that the doors are in the closed positions. If the at least one controller determines that the doors are in the closed positions as represented in a step 220, the controller then operates to cause the motor to cease operation as represented by step 222. However if the doors have not reached the door closed positions, the exemplary controller operates to wait another time increment for the calculation of a current velocity value. This is represented by step 224. After waiting the time increment for the calculation of the next velocity value, the at least one controller repeats the described operation to recalculate the current closing speed to make a determination if an obstruction has been encountered. Of course it should be understood that this logic flow is exemplary and is provided at a high schematic level. In other exemplary arrangements other approaches and steps may be carried out for purposes of determining if one of the doors has encountered an obstruction.

In exemplary arrangements the at least one controller may also operate to provide additional functions and capabilities in connection with the operation of the doors or other aspects of the bus. For example in an exemplary arrangement the at least one motion sensor 146 is operative to detect motion of the bus in which the door actuator 128 is positioned. In some exemplary arrangements the motion sensor may comprise a vibration or seismic sensor. Alternatively or in addition the motion sensor may be in operative connection with the transmission of the vehicle. In the exemplary arrangement the at least one controller 128 is operative to receive signals from the at least one motion sensor 146 that are usable to determine if the bus is in motion. The at least one controller operates to prevent the opening of the doors by the actuator if the bus is in motion. For example the controller may operate responsive to its circuit executable instructions to not cause the motor of the actuator to move the doors toward the open positions in circumstances where the motion sensor detects that the bus is in motion. In this way the exemplary controller operates to prevent inadvertent opening of the doors in the event that the at least one manually actuatable switch 140 is inadvertently or improperly operated while the bus is moving. Of course this approach is exemplary and other arrangements other approaches may be used.

In the exemplary arrangement the controller is operative to communicate wirelessly through the wireless portal 142 with the user mobile device 144. In exemplary arrangements the at least one data store 132 in operative connection with the at least one controller includes data corresponding to at least one authorized user access credential. The user access credential corresponds to at least one of an authorized user or an authorized user mobile device. In some exemplary arrangements the user access credential may correspond to one or more codes that can be input through at least one input device of the user mobile device. Such codes may include a secret code or PIN that is known only to the authorized user. In other exemplary arrangements the access credential may correspond to a biometric feature which may be read through operation of an input device on the user mobile device. This may include for example, a fingerprint that can be read through a fingerprint reader that is located on the user mobile device. Alternatively or in addition the biometric input may correspond to a facial image that may be captured through operation of the camera on the user mobile device. Alternatively the biometric input may correspond to voice data that may be sensed through a microphone of the mobile device. In other exemplary arrangements the user access credential may correspond to token data or other data that is stored in at least one data store of the user mobile device, which uniquely identifies the user mobile device. Numerous different types of user access credentials and/or combinations thereof may be utilized in exemplary arrangements.

The exemplary data store includes data that corresponds to or otherwise has a predetermined relationship with data corresponding to the user access credential that may be delivered wirelessly to the controller 128 from the user mobile device. Responsive to receipt of data from the user mobile device, the at least one controller is operative to make an authorized access determination responsive to the delivered data from the user mobile device having a predetermined relationship to the stored user access credential data. Responsive at least in part to the authorized access determination by the controller 128, the user mobile device is enabled to send wireless signals that are operative to cause the controller to operate certain devices of the bus. Alternatively or in addition, the user mobile device is enabled to receive communications which provide information to the user through the mobile device.

For example in some exemplary arrangements once the at least one controller 128 is operative to make the authorized access determination based on data sent from the user mobile device, the user mobile device may be operated by the bus driver from outside of the interior area of the bus to cause the controller to operate the actuator. In exemplary arrangements the user mobile device is enabled to communicate signals with the controller which cause the actuator to rotate the drive lever to change the doors between the door open positions and the door closed positions. As a result in exemplary arrangements the driver of the bus is enabled to exit the bus and through operation of the mobile device, cause the actuator to place the doors in the door closed positions. This enables the bus driver to leave the bus with the interior area thereof secured against unauthorized access. Further upon the return of the bus driver to the bus, or otherwise, the bus driver is enabled to communicate from the mobile device, wireless signals that cause the controller to operate the actuator so as to rotate the drive lever to move the doors from the closed positions to the open positions. Of course it should be understood that these approaches are exemplary, and in other arrangements other approaches may be used.

In other exemplary arrangements the at least one controller 128 may be operative to communicate wireless signals with the user mobile device corresponding to images that are captured by the cameras that are in operative connection with the controller. In exemplary arrangements the communication between the user mobile device and the at least one controller may be operative to communicate images that are in the field of view of the external area cameras 152. This may enable the bus driver user to determine if persons are in proximity to the vehicle who might be waiting to attack the bus driver. In other exemplary arrangements, the at least one controller may communicate wireless signals corresponding to images captured by the entry area camera or cameras 154. In exemplary arrangements communication of image data concerning the entry area cameras may be indicative of a person attempting to gain unauthorized access to the interior area of the bus. Alternatively or in addition, such image data that is transmitted to the user mobile device may show images of a person who is authorized to access the bus, but has arrived before the driver. In such circumstances the driver may wish to utilize the mobile device to send wireless signals to the controller to cause the doors to be in the open positions so that the person may access the interior area of the bus.

In some exemplary arrangements the at least one controller 128 may operate to provide wireless signals corresponding to image data for the field of view of the one or more interior area cameras 156. Such image data may be selectively viewed by the bus driver as outputs from the display of the user mobile device. Such outputs may enable the driver to observe activities in the interior area of the bus. This may include for example, activities of persons who remain in the interior area of the bus while the driver steps away for a short time. Alternatively or in addition, such image data may enable the bus driver to monitor the activities of persons that were allowed to enter the bus because they were recognized as authorized passengers before the bus driver arrived at the bus. Alternatively or in addition the images captured by interior area cameras may be utilized by the bus driver to determine if persons remained on the bus after the bus ceased operation or completed its normal route. This may be particularly effectively achieved by using cameras that provide night vision and/or object heat level sensing capabilities. In other exemplary arrangements the wireless communication of image data between the user mobile device and the at least one controller may be operative to help the bus driver verify that unauthorized persons are not present in the interior area the bus who may have gained unauthorized access and may be waiting to attack the driver. Numerous different approaches may be utilized in exemplary arrangements for purposes of enabling the driver or other authorized user of the user mobile device to monitor and control conditions at or in the bus.

Further in exemplary arrangements the at least one contamination sensor 148 may be usable to monitor conditions within the interior area of the bus. For example in some exemplary arrangements the at least one data store 132 may include data corresponding to a contamination threshold. Such a contamination threshold may correspond to a level of smoke, carbon monoxide, carbon dioxide or other contaminants that may correspond to an unacceptable level of the contaminant. In exemplary arrangements the at least one controller 128 is operative to monitor signals from the at least one contamination sensor 148 and to make a contamination determination based on the level of a contaminant reaching the stored contamination threshold, that an unacceptable level of a contaminant has been reached. In some exemplary arrangements the interior area of the bus may include at least one indicator which is operative to indicate to the driver while in the operating position, or to the other occupants of the bus, that the contamination level has reached an unacceptable level.

In some exemplary arrangements the at least one controller may operate responsive at least in part to the contamination determination to cause the bus to no longer be operable and to cause the actuator to automatically move the drive lever so as to open the doors. Such automatic opening of the doors will help to dissipate the contaminant level and also enable the passengers to more rapidly exit from the interior area of the vehicle. The exemplary controller may also operate in accordance with its programming to cause the audible annunciator 136 to output signals including warning signals and/or automated speech instructions advising users to immediately exit from the bus. Of course these approaches are exemplary and in other embodiments other approaches may be used.

Further in exemplary arrangements the at least one controller 128 may operate to send wireless signals to the user mobile device concerning contamination determinations. Thus for example in situations where the bus driver has left the engine of the bus running to maintain the heated condition of the interior area and/or the cool condition of the interior area, the controller may operate to send wireless signals to the user mobile device indicating that a contamination determination has been made. In exemplary arrangements the controller may be operative to include in the wireless signals data which causes the mobile device to output an indication to the bus driver as to the nature of the contamination determination. This may enable the bus driver to operate the mobile device to cause the doors to open to help dissipate the contamination. Further in alternative exemplary arrangements the at least one controller may operate to automatically cause the doors to be moved to the open positions in response to making the contamination determination. The controller may then operate to send wireless signals to the user mobile device to indicate the contamination determination as well as that the doors have been opened automatically to help minimize the potential problems associated with the excessive level of the contaminant. Of course it should be understood that these approaches are exemplary, and an alternative arrangements other approaches may be used.

In other exemplary arrangements different sensor devices may be in operative connection with the at least one controller 128. Such sensor devices may include devices such as temperature sensors, humidity sensors, lidar sensors, sonic sensors or other types of sensors that are usable to detect conditions, objects or persons within or in proximity to the bus. In exemplary arrangements wireless communications between the at least one controller and the user mobile device to be operative to advise the bus driver through the outputs from the user mobile device of conditions that the bus driver needs to be advised about while they are away from the bus. Further in exemplary arrangements the at least one controller may also operate to provide communications wirelessly with at least one computer in a command center or other monitoring facility associated with the entity responsible for operation of the bus. Such communications may be monitored at such a facility either automatically or by authorized users to identify circumstances which may warrant taking actions to preserve the health and safety of the bus driver or the passengers. As can be appreciated, numerous different aspects of conditions at or within the bus may be monitored for purposes of detecting and identifying potential problems or anomalous conditions. Of course these approaches are exemplary and in other arrangements other approaches and capabilities may be provided.

FIGS. 29-32 show a further alternative exemplary arrangement of an actuator 226. The exemplary actuator 226 is similar to actuator 28 previously described except as indicated hereafter. Actuator 226 includes a pneumatic motor rather than the electric motor that is used in actuator 28.

In the exemplary arrangement actuator 226 includes a drive lever 228. Drive lever 228 is rotatably movably mounted on a body 230 of the actuator in a manner similar to drive lever 34. Drive lever 228 is in operatively fixed connection with a shaft 232. Shaft 232 is in fixed operative connection with an upper cam 234 and a lower cam 236. Upper cam 234 is in operative connection with an upper cam switch 238. Lower cam 236 is in operative connection with a lower cam switch 240. In exemplary arrangements the upper cam and upper cam switch, and the lower cam and lower cam switch may be operative to detect and indicate the rotational position of the drive lever 228 in a manner like that previously described.

Actuator 226 further includes a pneumatic motor 242. Motor 242 comprises a pneumatic cylinder which includes an internal piston. A piston rod 244 is in operative connection with the piston and is selectively movable outside the cylinder responsive to the delivery and removal of air pressure from opposed sides of the piston within the cylinder. The piston rod includes an end link 246. The end link 246 is in operative rotatable connection with a crankshaft 248. The crankshaft 248 is in operative connection with the shaft 232.

In exemplary arrangements the actuator 226 includes adjustable air pressure regulator 250. The air pressure regulator enables the setting of the level of air pressure that is utilized for purposes of actuating the pneumatic motor/cylinder 242. The exemplary actuator further includes a solenoid valve 252. The exemplary solenoid valve is selectively operative responsive to electrical signals to cause air pressure to be selectively delivered to and released from each of the sides of the piston within the cylinder 242. Of course it should be understood that the regulator 250, the solenoid valve 252 and the ends of the cylinder 242 are fluidly connected through hoses or other suitable fluid conduits which are not shown.

The exemplary actuator 226 further includes an electrical enclosure 254 mounted thereon. The electrical enclosure includes circuitry associated with control of the actuator. The electrical enclosure 254 in some exemplary arrangements may house one or more controllers such as controller 128 previously discussed, or other types of circuitry associated with the actuator.

The exemplary actuator 226 further includes at least one shaft position sensor 256. In the exemplary arrangement the at least one shaft position sensor 256 is in operative connection with shaft 232 through an axial link 258. In this exemplary arrangement the axial link 258 rotates with the rotation of the shaft 232 which changes a voltage level output from the potentiometer 256 which varies with the rotational position of the shaft and the connected drive lever 228. As a result in this exemplary arrangement the signal corresponding to the voltage output from the potentiometer 256 can be correlated through operation of at least one controller with the rotational position of the drive lever.

The signals from the potentiometer may be utilized in a manner like that previously discussed to determine current closing speed and current opening speed of the doors. Further in this exemplary arrangement the upper and lower cams and associated cam switches may be operative to sense the rotational position of the drive lever in the door open positions and door closed positions respectively. Further in exemplary arrangements the associated sensors which include the cams may be operative to provide signals which can be utilized for calibration purposes with regard to signals that are generated by the shaft position sensor 256. For example, in the event that the signals from a potentiometer that is used as the shaft position sensor may change over time with wear or other factors, the at least one controller may operate to recalibrate its stored values to adjust for such changes in output values based on the set points where the cam switches determine that the doors are in the open and closed positions. Of course it should be understood that this approach is exemplary and in other arrangements other types of sensors and devices may be utilized for purposes of determining the position of the drive lever and the associated doors.

Thus the exemplary arrangements that have been described herein achieve improved operation, eliminate difficulties encountered in the use of prior devices and systems, and attain useful results described herein.

In the foregoing description, certain terms have been used for brevity, clarity and understanding. However no unnecessary limitations are to be implied therefrom because such terms are used for descriptive purposes and are intended to be broadly construed. Moreover the descriptions and illustrations herein are by way of examples, and the new and useful features and relationships are not limited to the exact features shown and described.

It should be understood that features and/or relationships associated with one arrangement can be combined with features and/or relationships from another arrangement. That is, various features and/or relationships from various arrangements can be combined to produce further arrangements. The new and useful scope of the disclosure is not limited only to the specific arrangements shown or described herein.

Having described features, discoveries and principles of the exemplary arrangements, the manner in which they are constructed and operated, and the advantages and useful results attained, the new and useful features, devices, elements, arrangements, parts, combinations, systems, equipment, operations, methods, processes and relationships are set forth in the appended claims.

We claim:

1. Apparatus comprising:
   a door actuator,
      wherein the door actuator is configured to move a pair of substantially planar doors,
      wherein each door is rotatable about a respective vertical door axis,
      wherein the vertical door axis of one door of the pair is horizontally disposed from the vertical door axis of the other door of the pair,
      wherein each door is rotatably movable about its respective vertical door axis between a door open position and a door closed position,
      wherein with each door in the door open position,
         each door is horizontally disposed from the other door of the pair, each door of the pair extends substantially parallel to the other door, such that the doors bound an open path between the doors through which individuals may pass,
wherein with each door of the pair in the door closed position,
each door is substantially linearly aligned with the other door,
each door is in contacting relation with the other door on a side of each door horizontally opposite of the respective vertical door axis, such that there is no path between the doors through which individuals may pass,
wherein the actuator includes
a body,
a drive lever, wherein the drive lever is rotatably mounted in operative connection with the body,
wherein the drive lever is configured to be in operative connection with each of the doors of the pair such that rotation of the drive lever is operative to cause each of the doors to move simultaneously in coordinated relation between the respective door open position and the respective door closed position,
a motor, wherein the motor is in operative supported connection with the body,
wherein the motor is in operative connection with the drive lever,
at least one sensor, wherein the at least one sensor is in operative connection with the drive lever,
a controller, wherein the controller includes circuitry, wherein the circuitry includes at least one data store, wherein the at least one data store includes data corresponding to a threshold closing speed,
wherein the controller is in operative connection with the motor and the at least one sensor,
wherein the controller is operative to cause the motor to move the drive lever from a first rotational position corresponding to the door open position of each of the doors of the pair, in a first rotational direction toward a second rotational position corresponding to the door closed position of each of the doors of the pair,
wherein the controller is operative at least in part to the at least one sensor to determine that a current closing speed of movement of the drive lever in the first rotational direction between the first and second rotational positions, is at least one of at or below the threshold closing speed,
wherein the controller is operative responsive at least in part to the determination to cause the motor to cease movement of the drive lever in the first rotational direction,
whereby engagement of at least one door with an obstruction when moving towards the respective door closed position causes the current closing speed to be at least one of at or below the threshold closing speed, such that door closing movement by the actuator is discontinued.

2. The apparatus according to claim
wherein the controller is operative responsive at least in part to the determination to cause the motor to move the drive lever in a second rotational direction opposed of the first rotational direction.

3. The apparatus according to claim 2
wherein responsive at least in part to the drive lever being sensed through operation of the at least one sensor as in the first rotational position, the controller is operative to cause the motor to stop movement of the drive lever in the second rotational direction.

4. The apparatus according to claim 3 wherein the at least one data store includes data corresponding to a threshold opening speed,
wherein the controller is operative to cause the motor to move the drive lever from the second rotational position in the second rotational direction toward the first rotational position,
wherein the controller is operative responsive at least in part to the at least one sensor to further determine that the current opening speed of the drive lever in the second rotational direction between the second rotational position and first rotational position, is at least one of at or below the threshold opening speed,
wherein the controller is operative responsive at least in part to the further determination to cause the motor to cease moving the drive lever in the second rotational direction,
whereby engagement of at feast one door with an obstruction in moving between the respective door closed position toward the respective door open position is operative to cause the doors to discontinue movement toward the door open positions.

5. The apparatus according to claim 4
wherein the at least one sensor comprises at least one of
a potentiometer,
an optical encoder,
a cam,
a Hall Effect sensor,
an inductance sensor, and
a magnetic sensor.

6. The apparatus according to claim 5
wherein the controller is operative to calculate at least one of the current closing speed and the current opening speed as a function of drive lever speed in each of a plurality of different angular positions.

7. The apparatus according to claim 5
wherein the controller is operative to calculate at least one of the current closing speed and the current opening speed as an average of drive lever speed in each of a plurality of different angular positions.

8. The apparatus according to claim 5
wherein the motor comprises at least one of an electric motor and a pneumatic cylinder.

9. The apparatus according to claim 8
wherein the actuator further includes a manually movable lever, wherein the manually movable lever is movably mounted in operatively supported connection with the body,
wherein the manually movable lever is in operative connection with at least one of the motor and the drive lever,
wherein manual movement of the manually movable lever to an engagement position is operative to cause the motor and the drive lever to be in operative engagement, wherein manual movement of the manually movable lever to a disengagement position is operative to cause the motor and the drive lever to be operatively disengaged,
whereby when the manually movable lever is in the disengagement position, the drive lever and each of the doors in engagement therewith are manually movable between the door open positions and the door closed positions without the actuator preventing such movement.

10. The apparatus according to claim 9
wherein the actuator further comprises a slide, wherein the slide is movably mounted in operatively supported connection with the body,
wherein the motor is operatively engaged with the slide,
wherein the manually movable lever is in operative engagement with the slide such that when the manually movable lever is in the engagement position the slide is in a first slide position relative to the body, and when the manually movable lever is in the disengagement position the slide is in a second slide position relative to the body, wherein the first slide position is disposed from the second slide position.

11. The apparatus according to claim 9
and further comprising an audible annunciator,
wherein the audible annunciator is in operative connection with the controller,
wherein the controller is operative to cause the audible annunciator to output an audible signal responsive at least in part to at least one of
 the determination that the current closing speed is at least one of less than or equal to the threshold closing speed, and
 the further determination that the current opening speed is at least one of less than or equal to the threshold opening speed.

12. The apparatus according to claim 11
and further comprising a wireless portal, wherein the wireless portal is in operative connection with the controller,
wherein the controller is operative responsive at least in part to wireless communication with a user mobile device through the wireless portal to cause at least one of
 the motor to cause the drive lever to move from the first rotational position to the second rotational position, whereby the doors are each in the respective open position, and
 the motor to cause the drive lever to move from the second rotational position to the first rotational position, whereby the doors are each in the respective closed position.

13. The apparatus according to claim 12
and further comprising at least one camera interface, wherein the at least one camera interface is in operative connection with the controller, wherein the at least one camera interface is connectable to at least one entry area camera with a field of view of an entry area adjacent to the doors,
wherein the controller is operative to communicate through the wireless portal with the user mobile device, signals corresponding to images of the field of view of the entry area such that the images may be output through the user mobile device.

14. The apparatus according to claim 13
wherein the at least one camera interface is connectable with at least one interior area camera, wherein the at least one interior area camera has a field of view of an interior area of a vehicle to which access is controlled through operation of the doors,
wherein the controller is operative to communicate through the wireless portal with the user mobile device, signals corresponding to images of the field of view of the interior area camera such that the images may be output through the user mobile device.

15. The apparatus according to claim 14
wherein the at least one camera interface is connectable with at least one external area camera having a field of view of an external area adjacent to the vehicle,
wherein the controller is operative to communicate through the wireless portal with the user mobile device, signals corresponding to images of the field of view of the external area such that the images may be output through the user mobile device.

16. The apparatus according to claim 15
and further comprising a motion sensor, wherein the motion sensor is in operative connection with the controller, wherein the motion sensor is operative to detect motion of the vehicle,
wherein the controller is operative to prevent movement of the drive lever responsive at least in part to motion sensor detected motion of the vehicle.

17. The apparatus according to claim 16
and further comprising a contamination sensor, wherein the contamination sensor comprises at least one of
 a carbon monoxide sensor,
 a carbon dioxide sensor, and
 a smoke sensor,
wherein the contamination sensor is in operative connection with the controller,
wherein the at least one data store includes data corresponding to a contamination threshold,
wherein the controller is operative responsive at least in part to contamination sensed by the contamination sensor to make a contamination determination that contamination has reached the contamination threshold, wherein the controller is operative responsive at least in part to the contamination determination to communicate wireless messages through the wireless portal with the user mobile device indicative of the sensed contamination.

18. The apparatus according to claim 17
wherein the controller is operative to cause the motor to move the drive lever to the second rotational position responsive at least in part to the contamination determination, whereby each of the doors is in the respective door open position.

19. The apparatus according to claim 17
wherein at least one camera among
 the at least one entry area camera,
 the at least one interior area camera, and
 the at least one external area camera
comprises at least one of
 a night vision camera, and
 a heat detecting camera.

20. The apparatus according to claim 17
wherein the at least one data store includes data corresponding to at least one user access credential, wherein the at least one user access credential corresponds to at least one of an authorized user and an authorized user mobile device,
wherein the controller is operative to receive through the wireless portal, wireless messages including identifying data from the user mobile device,
wherein the controller is operative to make an authorized access determination responsive at least in part to the identifying data having a predetermined relationship with the at least one user access credential,
wherein responsive at least in part to the authorized access determination the controller is operative to cause the motor to move the drive lever responsive to communication with the user mobile device.

21. The apparatus according to claim 20
and further comprising a manually actuatable switch, wherein the manually actuatable switch is located within the interior area of the vehicle,
wherein the manually actuatable switch is in operative connection with the controller,
wherein manual actuation of the manually actuatable switch is operative to cause the controller to cause the motor to move the drive lever between the first rotational position and the second rotational position.

22. The apparatus according to claim 21
and further comprising the vehicle, wherein the vehicle comprises a bus.

23. The apparatus according to claim 1
wherein responsive at least in part to the drive lever being sensed through operation of the at least one sensor as in the second rotational position, the controller is operative to cause the motor to stop movement of the drive lever in the first rotational direction.

24. The apparatus according to claim 1
wherein the motor comprises a pneumatic cylinder.

25. The apparatus according to claim 1
wherein the actuator further includes a manually movable lever, wherein the manually movable lever is movably mounted in operatively supported connection with the body,
wherein the manually movable lever is in operative connection with at least one of the motor and the drive lever,
wherein manual movement of the manually movable lever to an engagement position is operative to cause the motor and the drive lever to be in operative engagement, and wherein manual movement of the manually movable lever to a disengagement position is operative to cause the motor and the drive lever to be operatively disengaged,
whereby when the manually movable lever is in the disengagement position, the drive lever and each of the doors in engagement, therewith are each manually movable between the respective door open position and the respective door closed position without the actuator preventing such manual movement.

26. The apparatus according to claim 1
and further comprising at least one of an audible annunciator and a visual indicator, wherein the at least one audible annunciator and visual indicator is in operative connection with the controller,
wherein the controller is operative to cause the at least one of the audible annunciator and visual indicator to output a signal responsive at least in part to the determination that the current closing speed is at least one of less than or equal to the threshold closing speed.

27. The apparatus according to claim 1
and further comprising a wireless portal, wherein the wireless portal is in operative connection with the controller,
wherein the controller is operative responsive at least in part to wireless communication with a user mobile device through the wireless portal to cause at least one of
the motor to cause the drive lever to move from the first rotational position to the second rotational position, whereby each of the doors is in the respective door open position, and
the motor to cause the drive lever to move from the second rotational position to the first rotational position, whereby each of the doors is in the respective door closed position.

28. The apparatus according to claim 1
and further comprising:
a wireless portal, wherein the wireless portal is in operative connection with the controller,
at least one camera interface, wherein the at least one camera interface is in operative connection with the controller, wherein the at least one camera interface is operatively connectable to at least one camera having a field of view that includes at least one of an entry area adjacent to the doors, an interior area of a vehicle to which access is controlled by the doors, and an external area adjacent to the vehicle,
wherein the controller is operative to communicate through the wireless portal with a user mobile device, signals corresponding to images of the field of view such that the images may be output through the user mobile device.

29. The apparatus according to claim 1
and further comprising a motion sensor, wherein the motion sensor is in operative connection with the controller,
wherein the controller is operative responsive at least in part to the motion sensor to cause the controller to prevent movement of the drive lever when motion is detected by the motion sensor.

30. The apparatus according to claim 1
and further comprising a contamination sensor, wherein the contamination sensor comprises at least one of
a carbon monoxide sensor,
a carbon dioxide sensor, and
a smoke sensor
wherein the contamination sensor is in operative connection with the controller,
wherein the at least one data store includes data corresponding to a contamination threshold,
wherein the controller is operative responsive at least in part to contamination sensed by the contamination sensor to make a contamination determination that contamination has reached the contamination threshold,
wherein the controller is operative responsive at least in part to the contamination determination to cause at least one of
an output through at least one audible annunciator or visual indicator,
at least one wireless message to be sent responsive to operation of the controller to at least one user mobile device, and
the motor to cause the drive lever to move to the second rotational position, whereby the each of the doors is in the respective door open position.

31. Apparatus comprising:
a door actuator,
wherein the door actuator is configured to move a pair of substantially planar doors,
wherein each door is rotatable about a respective vertical door axis,
wherein the vertical door axis of one door of the pair is horizontally disposed from the vertical door axis of the other door of the pair, wherein each door is rotatably movable about its respective vertical door axis between a respective door open position and a respective door closed position, wherein with each door in the door open position,
each door is horizontally disposed from the other door of the pair, and
each door of the pair extends substantially parallel to the other door, such that the doors bound an open path between the doors through which individuals may pass, wherein with each door of the pair in the door closed position,
each door is substantially lineally aligned with the other door, and
each door is in contacting relation with the other door on a respective side of each door horizontally opposite of the respective vertical door axis, such that there is no path between the doors through which individuals may pass, wherein the actuator includes
a body,
a drive lever, wherein the drive lever is rotatably mounted in operative connection with the body,
wherein the drive lever is configured to be in operative connection with each of the doors of the pair such that rotation of the drive lever is operative to cause each of the doors to move simultaneously in coordinated relation between the respective door open position and the respective door closed position,
a motor, wherein the motor is in operative supported connection with the body,
wherein the motor is in operative connection with the drive lever,
at least one sensor, wherein the at least one sensor is in operative connection with the drive lever,
a controller, wherein the controller includes circuitry,
wherein the controller is in operative connection with the motor and the at least one sensor,
wherein the controller is operative to cause the motor to move the drive lever from a first rotational position corresponding to the door open position of each of the doors of the pair, in a first rotational direction toward a second rotational position corresponding to the door closed position of each of the doors of the pair,
wherein the controller is operative
responsive at least in part to the at least one sensor, to calculate at least one current rotational closing speed of the drive lever during movement in the first rotational direction intermediate of the first rotational position and the second rotational position,
to compare the at least one current rotational closing speed and a threshold closing speed,
to determine the at least one current rotational speed is not in excess of the threshold closing speed,
responsive to at least in part to the determination, to cause the motor to cease movement of the drive lever in the first rotational direction,
whereby engagement of at least one door with an obstruction when moving towards the respective door closed position causes door closing movement by the actuator to be discontinued.

32. The apparatus according to claim 31
wherein the controller is operative to calculate the at least one current closing speed as a function of the drive lever speed in each of a plurality of different angular positions.

33. The apparatus according to claim 31
wherein the actuator further includes a manually movable lever, wherein the manually movable lever is movably mounted in operatively supported connection with the body,
wherein the manually movable lever is in operative connection with at least one of the motor and the drive lever,
wherein with the manually movable lever in an engagement position, the motor and the drive lever are operatively engaged such that motor operation causes movement of the drive lever, and
wherein with the manually movable lever in a disengagement position, the motor and the drive lever are operatively disconnected, and wherein manual movement of each door of the pair of doors between the door open position and the door closed position is not prevented by the drive.

34. The apparatus according to claim 31
wherein the controller is further operative
responsive at least in part to the determination to cause the drive lever to rotate in a second rotational direction opposed of the first rotational direction,
to compare at least one door opening speed of the drive lever in the second rotational direction and a door opening threshold speed,
to make a further determination that the at least one door opening speed is not in excess of the door opening threshold speed,
responsive at least in part to the further determination to cause motor operation to cease moving the drive lever in the second rotational direction.

* * * * *